US009549928B2

(12) United States Patent
Messer et al.

(10) Patent No.: US 9,549,928 B2
(45) Date of Patent: *Jan. 24, 2017

(54) MUSCARINIC AGONISTS AS ENHANCERS OF COGNITIVE FLEXIBILITY

(75) Inventors: William S. Messer, Toledo, OH (US); Michael Ragozzino, Chicago, IL (US)

(73) Assignees: THE UNIVERSITY OF TOLEDO, TOLEDO, OH (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 361 days.

This patent is subject to a terminal disclaimer.

(21) Appl. No.: 14/114,646

(22) PCT Filed: Apr. 30, 2012

(86) PCT No.: PCT/US2012/035775
§ 371 (c)(1),
(2), (4) Date: Dec. 2, 2013

(87) PCT Pub. No.: WO2012/149524
PCT Pub. Date: Nov. 1, 2012

(65) Prior Publication Data
US 2014/0088119 A1  Mar. 27, 2014

Related U.S. Application Data

(60) Provisional application No. 61/481,150, filed on Apr. 29, 2011, provisional application No. 61/510,570, filed on Jul. 22, 2011.

(51) Int. Cl.
*A61K 31/506* (2006.01)
*A61K 31/00* (2006.01)

(52) U.S. Cl.
CPC ............. *A61K 31/506* (2013.01); *A61K 31/00* (2013.01)

(58) Field of Classification Search
None
See application file for complete search history.

(56) References Cited

U.S. PATENT DOCUMENTS

| | | | |
|---|---|---|---|
| 4,652,641 A | 3/1987 | Parsons |
| 4,710,508 A | 12/1987 | Bergmeier et al. |
| 4,786,648 A | 11/1988 | Bergmeier et al. |
| 5,041,455 A | 8/1991 | Sauerberg et al. |
| 5,086,053 A | 2/1992 | Brodin et al. |
| 5,175,166 A | 12/1992 | Dunbar et al. |
| 5,284,859 A | 2/1994 | Sauerberg et al. |
| 5,403,845 A | 4/1995 | Dunbar et al. |
| 5,414,009 A | 5/1995 | Olesen et al. |
| 5,424,305 A | 6/1995 | Skalkos et al. |
| 5,512,559 A | 4/1996 | Skalkos et al. |
| 5,571,826 A | 11/1996 | Sauerberg et al. |
| 5,618,818 A | 4/1997 | Ojo et al. |
| 5,712,297 A | 1/1998 | Sauerberg et al. |
| 5,718,912 A | 2/1998 | Thomspon et al. |
| 5,726,179 A | 3/1998 | Messer, Jr. et al. |
| 5,744,598 A | 4/1998 | Skalkos et al. |
| 5,852,037 A | 12/1998 | Bodick et al. |
| 6,040,442 A | 3/2000 | Merritt et al. |
| 6,096,767 A | 8/2000 | Rajeswaran et al. |
| 6,162,791 A | 12/2000 | Karimian et al. |
| 6,211,204 B1 | 4/2001 | Messer et al. |
| 6,255,540 B1 | 7/2001 | Erhardt et al. |
| 6,369,081 B1 | 4/2002 | Rajeswaran et al. |
| 6,376,675 B2 | 4/2002 | Messer et al. |
| 6,602,891 B2 | 8/2003 | Messer et al. |
| 7,265,246 B2 | 9/2007 | Allen et al. |
| 7,273,857 B2 | 9/2007 | Kelly et al. |
| 7,291,611 B2 | 11/2007 | Kelly et al. |
| 7,300,928 B2 | 11/2007 | Kelly et al. |
| 7,326,731 B2 | 2/2008 | Allen et al. |
| 7,361,668 B2 | 4/2008 | Guyaux et al. |
| 2001/0036953 A1 | 11/2001 | Messer |
| 2003/0032658 A1 | 2/2003 | Messer et al. |
| 2003/0069290 A1 | 4/2003 | Wishka et al. |
| 2007/0049576 A1 | 3/2007 | Barlow et al. |
| 2008/0009520 A1 | 1/2008 | Kelly et al. |
| 2008/0032965 A1 | 2/2008 | Hirst et al. |
| 2008/0108618 A1 | 5/2008 | Brann et al. |
| 2009/0012101 A1 | 1/2009 | Messer, Jr. et al. |

FOREIGN PATENT DOCUMENTS

| | | |
|---|---|---|
| CA | 2113424 | 3/1993 |
| CA | 2434839 | 8/2002 |
| EP | 0060244 B1 | 9/1982 |
| EP | 0239309 B1 | 9/1987 |
| EP | 0244018 B1 | 11/1987 |
| EP | 0259621 A2 | 3/1988 |

(Continued)

OTHER PUBLICATIONS

U.S. Appl. No. 14/056,616, filed Oct. 2013, Messer*
Messer et al., Development of CDD-0102A as a Selective M1 agonist for the Treatment of Alzheimer's Disease, Drug Development Research, vol. 57, p. 200-213, 2002.*
Messer et al., Pharmaceutica Acta Helvetiae 74 (2000) 135-140.*
Messer et al., Drug Development Research 40: 171-184 (1997).*
Messer et al., J. Med. Chem. 1997, 40- 1230-1246.*
Messer et al., P2-448: Preclinical evaluation of CDD-0102, a selective M1 agonist with potential utility in Alzheimer's disease, Jul. 2008, vol. 4, Issue 4, Supplement, p. T505.*
Swain et al., Tourette's syndrome in children, Current Treatment Options in Neurology, Jul. 2003, vol. 5, Issue 4, pp. 299-308.*
Canadian Office Action, Application No. 2,434,839 dated Jan. 19, 2009.

(Continued)

*Primary Examiner* — Svetlana M Ivanova
(74) *Attorney, Agent, or Firm* — MacMillan, Sobanski & Todd, LLC

(57) ABSTRACT

Methods and compositions for treating a mental condition in a subject in need thereof, includes administering to a subject in need thereof an effective amount of a CDD-102A compound [5-(3-ethyl-1,2,4-oxadiazol-5-yl)-1,4,5,6-tetrahydropyrimidine], or a pharmaceutically acceptable salt or hydrate thereof pharmaceutically acceptable salt or hydrate thereof.

10 Claims, 12 Drawing Sheets

(56) References Cited

FOREIGN PATENT DOCUMENTS

| EP | 0296721 A2 | 12/1988 | | |
|---|---|---|---|---|
| EP | 0307142 B1 | 3/1989 | | |
| EP | 0316718 B1 | 5/1989 | | |
| EP | 0349956 A1 | 1/1990 | | |
| EP | 0384285 A2 | 8/1990 | | |
| EP | 0384288 A2 | 8/1990 | | |
| EP | 0459568 A2 | 12/1991 | | |
| EP | 0630244 B1 | 12/1999 | | |
| EP | 1355646 B1 | 10/2003 | | |
| WO | 92/03430 A1 | 3/1992 | | |
| WO | 93/03726 A1 | 3/1993 | | |
| WO | WO 9303726 A1 * | 3/1993 | ........... | C07D 211/78 |
| WO | 93/14089 A1 | 7/1993 | | |
| WO | 94/20495 A1 | 9/1994 | | |
| WO | 94/20496 A1 | 9/1994 | | |
| WO | 95/05379 A1 | 2/1995 | | |
| WO | 96/13167 A1 | 5/1996 | | |
| WO | 98/46231 A1 | 10/1998 | | |
| WO | 02/060444 A1 | 8/2002 | | |
| WO | 2007/075297 A2 | 7/2007 | | |
| WO | 2008/118326 A1 | 10/2008 | | |

OTHER PUBLICATIONS

European Examination Report, Application No. 01995477.5 dated Jun. 12, 2007.
European Examination Report, Application No. 92919345.6 dated Jun. 5, 1997.
European Examination Report, Application No. 01995477.5 dated Jun. 20, 2006.
Japanese Notificaiton of Reasons for Rejection, Application No. 5-504463 dated Dec. 12, 2000.
Japanese Notificaiton of Reasons for Rejection, Application No. 2001-175844 dated Jun. 30, 2003.
Japanese Notification of Reasons for Rejection, Application No. 2002-560636 dated Nov. 18, 2009.
Japanese Notification of Reasons for Rejection, Application No. 2002-560636 dated Jun. 27, 2008.
Japanese Notification of Reasons for Rejection, Application No. 5-504463 dated Sep. 24, 2002.
PCT International Preliminary Report on Patentability, Application No. PCT/US2009/043935 filed May 14, 2009, dated Nov. 25, 2010.
PCT International Preliminary Report on Patentability, Application No. PCT/US1992/006842 filed Aug. 3, 1992, dated Nov. 5, 1993.
PCT International Preliminary Report on Patentability, Application No. PCT/US2006/046840 filed Dec. 8, 2006, dated Jul. 1, 2008.
PCT International Preliminary Report on Patentability, Application No. PCT/US2001/047474 filed Dec. 10, 2001, dated May 2, 2003.
PCT International Search Report and the Written Opinion, Application No. PCT/US2009/043935 filed May 14, 2009, dated Jun. 25, 2009.
PCT International Search Report and the Written Opinion, Application No. PCT/US2006/046840 filed Dec. 8, 2006, dated Nov. 23, 2007.
PCT International Search Report and the Written Opinion, Application No. PCT/US2009/047124 filed Jun. 11, 2009, dated Dec. 3, 2009.
PCT International Search Report and the Written Opinion, Application No. PCT/US2008/003637 filed Mar. 20, 2008, dated Jun. 20, 2008.
Abood et al., "Anticholinergic Psychotomimetic Agents", International Review of Neurobiology, 1962, vol. 4, pp. 217-273.
Anagnostaras et al., "Selective Cognitive Dysfunction in Acetylcholine M1 Muscarinic Receptor Mutant Mice", Nature Neuroscience, 2003, vol. 6, No. 1, pp. 51-58.
Baumeister et al., "Historical Development of the Dopamine Hypothesis of Schizophrenia", Journal of the History of the Neurosciences, 2002, vol. 11, No. 3, pp. 265-277.
Beers et al., "Structure and Activity of Acetylcholine", Nature, 1970, vol. 228, pp. 917-922.
Bodick et al., "Effects of Xanomeline, a Selective Muscarinic Receptor Agonist, on Cognitive Function and Behavioral Symptoms in Alzheimer Disease", Archives of Neurology, 1997, vol. 54, pp. 465-473.
Bodick et al., "The Selective Muscarinic Agonist Xanomeline Improves Both the Cognitive Deficits and Behavioral Symptoms of Alzheimer Disease", Alzheimer Disease and Associated Disorders, 1997, vol. 11, Supplement 4, pp. S16-S22.
Bosin et al., "Routes to Functionalized Guandidines. The Synthesis of Guanidino Diesters", Journal of Organic Chemistry, 1973, vol. 38, No. 8, p. 1591.
Brimblecombe et al., "The Synthesis & Pharmacology of Some 1,4,5,6,—Tetrahydropyrimidines", British Journal of Pharmacology, 1969, vol. 37, No. 2, pp. 425-435, Abstract Only.
Cao et al., "Synthesis and Biological Characterization of 1-Methyl-1,2,5,6-tetrahydropyridyl-1,2,5-thiadiazole Derivatives as Muscarinic Agonists for the Treatment of Neurological Disorders", Journal of Medicinal Chemistry, 2003, vol. 46, pp. 4273-4286.
Carlsson et al., "Interactions Between Monoamines, Glutamate, and GABA in Schizophrenia: New Evidence", Annual Review of Pharmacology and Toxicology, 2001, vol. 41, pp. 237-260.
Carlsson, "The Current Status of the Dopamine Hypothesis of Schizophrenia", Neuropsychopharmacology, 1988, vol. 1, No. 3, pp. 179-186.
Christopoulos et al., "Synthesis and Pharmacological Evaluation of Dimeric Muscarinic Acetylcholine Receptor Agonists", The Journal of Pharmacology and Experimental Therapeutics, 2001, vol. 298, No. 3, pp. 1260-1268.
Cummings et al., "The Cholinergic Hypothesis of Neuropsychiatric Symptoms in Alzheimer's Disease", American Journal of Geriatric Psychiatry, 1998, vol. 6, No. 2, pp. S64-S78.
Cummings, "The Role of Cholinergic Agents in the Management of Behavioral Disturbances in Alzheimer's Disease", International Journal of Neurophyschopharmacology, 2000, vol. 3, Supplement 2, pp. S21-S29.
Dean, "M1 Receptor Agonism, A Possible Treatment for Cognitive Deficits in Schizophrenia", Neuropsychopharmacology, 2004, vol. 29, pp. 1583-1584.
Dunbar et al., "Design, Synthesis, and Neurochemical Evaluation of 5-(3-Alkyl-1,2,4-oxadiazol-5-yl)-1,4,5,6-tetrahydropyrimidines as m1 Muscarinic Receptor Agonists", Journal of Medicinal Chemistry, 1993, vol. 36, No. 7, pp. 842-847.
Dunbar et al., "Design, Synthesis and Neurochemical Evaluation of 2-Amino-5-(alkoxycarbonyl)-3,4,5,6-Tetrahydropyridence and 2-Amino-5-(alkoxycarbonyl)-1,4,5,6-tetrahydropyridines as M1 Muscarinic Receptor Agonists", Journal of Medicinal Chemistry, 1994, vol. 37, p. 2774.
Felder et al., "Elucidating the Role of Muscarinic Receptors in Psychosis", Life Sciences, 2001, vol. 68, pp. 2605-2613.
Fenton et al., "Breaking the Log-Jam in Treatment Development for Cognition in Schizophrenia: NIMH Perspective", Psychopharmacology, 2003, vol. 169, pp. 365-366.
Fisher et al., "(±)-cis-2-Methyl-Spiro (1,3-Oxathiolane-5,3')Quinuclidine, an M1 Selective Cholinergic Agonist, Attenuates Cognitive Dysfunctions in an Animal Model of Alzheimer's Disease", The Journal of Pharmacology and Experimental Therapeutics, 1991, vol. 257, No. 1, pp. 392-403.
Fisher et al., "±cis-2-methylspiro (1,3-oxathiolane-5,3')quinuclidine (AF102B): A New M1 Agonist Attenuates Cognitive Dysfunctions in Af64A-Treated Rats", Neuroscience Letters, 1989, vol. 102, pp. 325-331, Abstract Only.
Freedman et al., "A Novel Series of Non-Quaternary Oxadiazoles Acting as Full Agonists at Muscarinic Receptors", British Journal of Pharmacology, 1990, vol. 101, pp. 575-580.
Friedman et al., "Pharmacologic Strategies for Augmenting Cognitive Performance in Schizophrenia", Society of Biological Psychiatry, 1999, vol. 45, pp. 1-16.
Greenhalgh et al., "Acetylation of Some Alkyl-Substituted Guanidines With Acetic Anhydride and Ethyl Acetate", Canadian Journal of Chemistry, 1961, vol. 39, pp. 1017-1029.
Harries et al., "The Profile of Sabcomeline (SB-202026), A Functionally Selective M1 Receptor Partial Agonist, In the Marmoset", British Journal of Phamacology, 1998, vol. 124, pp. 409-415.

(56) References Cited

OTHER PUBLICATIONS

Hatcher et al., "Sabcomeline (SB-202026), A Functionally Selective M1 Receptor Partial Agonist, Reverses Delay-Induced Deficits in the T-Maze", Psychopharmacology, 1998, vol. 138, pp. 275-282.
Hyman et al., "What are the Right Targets for Psychopharmacology?", Science, 2003, vol. 299, pp. 350-351.
Iadanza et al., "κ-Opioid Receptor Model in a Phospholipid Bilayer: Molecular Dynamics Simulation", Journal of Medicinal Chemistry, 2002, vol. 45, pp. 4838-4846.
Jeppesen et al., "1- (1,2,5-Thiadiazol-4-yl)-4-azatricyclo[2.2.1.02,6]heptanes as New Potent Muscarinic M1 Agonists: Structure-Activity Relationship for 3-Aryl-2-propyn-1-yloxy and 3-Aryl-2-propyn-l-ylthio Derivatives", Journal of Medicinal Chemistry, 1999, vol. 42, pp. 1999-2006.
Jones et al., "Effects of Scopolamine in Comparison with Apomorphine and Phencyclidine on Prepulse Inhibition in Rats", European Journal of Pharmacology, 2000, vol. 391, pp. 105-112.
Jones et al., "Muscarinic Cholinergic Modulation of Prepulse Inhibition of the Acoustic Startle Reflex", The Journal of Pharmacology and Experimental Therapeutics, 2000, vol. 294, No. 3, pp. 1017-1023.
Kelleher et al., "Advances in Atypical Antipsychotics for the Treatment of Schizophrenia", CNS Drugs, 2002, vol. 16, No. 4, pp. 249-261.
Langmead et al., "Muscarinic Acetylcholine Receptors as CNS Drug Targets", Pharmacology & Therapeutics, 2008, vol. 117, pp. 232-243.
Leung-Toung et al., "1,2,4-Thiadiazole: A Novel Cathepsin B. Inhibitor", Bioorganic & Medicinal Chemistry, 2003, vol. 11, No. 24, pp. 5529-5537, Abstract Only.
Levey, "Muscarinic Acetylcholine Receptor Expression in Memory Circuits: Implications for Treatment of Alzheimer's Disease", Proceedings of the National Academy of Sciences (PNAS), 1996, vol. 93, pp. 13456-13541.
Levy et al., "Neuropsychiatric Symptoms and Cholinergic Therapy for Alzheimer's Disease", Gerontology, 1999, vol. 41, Supplement 1, pp. 15-22.
MacLeod et al., "Synthesis and Muscarinic Activities of 1,2,4-Thiadiazoles", Journal of Medicinal Chemistry, 1990, vol. 33, No. 7, pp. 2052-2059.
Messer, Jr. et al., "Synthesis and Biological Characterization of 1,4,5,6-Tetrahydropyrimidine and 2-Amino-3,4,5,6-Tetrahydropyridine Derivatives as Selective m1 Agonists", Journal of Medicinal Chemistry, 1997, vol. 40, No. 8, pp. 1230-1246.
Messer, Jr. et al., "Synthesis, Biochemical Activity and Behavioral Effects of a Series of 1,4,5,6-Tetrahydropyrimidines as Novel Ligands for M1 Receptors", Bioorganic & Medicinal Chemistry Letters, 1992, vol. 2, No. 8, pp. 781-786.
Messer, Jr., et al., "Tetrahydroprimidine Derivatives Display Functional Selectivity for M1 Muscarinic Receptors in Brain", Drug Development Research, 1997, vol. 40, pp. 171-184.
Messer, Jr., et al., "Design and Development of Selective Muscarinic Agonists for the Treatment of Alzheimer's Disease: Characterization of Tetrahydropyrimidine Derivatives and Development of New Approaches for Improved Affinity and Selectivity for M1 Receptors", Pharmaceutica Acta Helvetiae, 2000, vol. 74, pp. 135-140.
Messer, Jr., et al., "Development of CDD-0102 as a Selective M1 Agonist for the Treatment of Alzheimer's Disease", Drug Development Research, 2002, vol. 57, pp. 200-213.
Moos et al., "Cholinergic Agents: Effect of Methyl Substitution in a Series of Arecoline Derivatives on Binding to Muscarinic Acetylcholine Receptors", Journal of Pharmaceutical Sciences, 1992, vol. 81, No. 10, pp. 1015-1019.
Olesen et al., "3-(3-Alkylthio-1,2,5-Thiadiazole-4-yl)-1-Azabicycles. Structure-Activity Relationships for Antinociception Mediated by Central Muscarinic Receptors", European Journal of Medicinal Chemistry, 1996, vol. 31, No. 3, pp. 221-230, Abstract Only.
Olesen et al., "Preparation of Heterocyclic Compounds as Muscarinic Agonists", Heterocycles, 1994, vol. 120, p. 1167, Abrstact Only.
Olesen et al., "Synthesis and Structural Determination of Stereoisomers of Muscarinic Ligands of the (3-Propylthio-1,2,5-Thiadiazole-4-yl)-1-Azabicycloalkane Type", Chirality, 1997, vol. 9, No. 8, pp. 739-749, Abstract Only.
Orlek et al., "Comparison of Azabicyclic Esters and Oxadiazoles as Ligands for the Muscarinic Receptor", Journal of Medicinal Chemistry, 1991, vol. 34, No. 9, pp. 2726-2735.
Rajeswaran et al., "Design, Synthesis, and Biological Characterization of Bivalent 1-Methyl-1,2,5,6-tetrahydropyridyl-1,2,5-thiadiazole Derivatives as Selective Muscarinic Agonists", Journal of Medicinal Chemistry, 2001, vol. 44, No. 26, pp. 4563-4576.
Ranney et al., "The Pharmacological Actions of Some Guanidine Esters and Their Relationship to Tetrodotoxin", Archives Internationales de Pharmacodynamie et de Thérapie, 1968, vol. 175, No. 1, pp. 193-211.
Rasmussen et al., "The Muscarinic Receptor Agonist BuTAC, a Novel Potential Antipsychotic, Does Not Impair Learning and Memory in Mouse Passive Avoidance", Schizophrenia Research, 2001, vol. 49, pp. 193-201.
Sauerberg et al., "Muscarinic Agonists with Antipsychotic-like Activity: Structure-Activity Relationships of 1,2,5- Thiadiazole Analogues with Functional Dopamine Antagonist Activity", Journal of Medicinal Chemistry, 1998, vol. 41, No. 22, pp. 4378-4384.
Sauerberg et al., "Muscarinic Cholinergic Agonists and Antagonists of the 3-(3-Alkyl-1,2,4-oxadiazol-5-yl)-1,2,5,6-tetrahydropyridine Type, Synthesis & Structure-Activity Relationships", Journal of Medicinal Chemistry, 1991, vol. 34, No. 2, pp. 687-692.
Sauerberg et al., "Novel Functional M1 Selective Muscarinic Agonists. Synthesis and Structure-Activity Relationships of 3-(1,2,5-Thiadiazolyl)-1,2,5,6-tetrahydro-1-methylpyridines", Journal of Medicinal Chemistry, 1992, vol. 35, No. 12, pp. 2274-2283.
Sauerberg et al., "Synthesis and Structure-Activity Relationships of Heterocyclic Analogues of the Functional M1 Selective Mescarinic Agonist Hexyloxy-TZTP", Bioorganic and Medicinal Chemistry Letters, 1992, vol. 2, No. 8, pp. 809-814, Abstract Only.
Saunders et al., "2-Methyl-1, 3-Dioxazaspiro [4.5] Decanes as Novel Muscarinic Cholinergic Agonist", Journal of Medicinal Chemistry, 1988, vol. 31, No. 2, pp. 486-491.
Saunders et al., "Ester Bio-isosteres: Synthesis of Oxadiazolyl-1-azabicyclo[2.2.1] Heptanes as Muscarinic Agonist", Journal of the Chemical Society, Chemical Communications, 1988, pp. 1618-1619.
Saunders et al., "Novel Quinuclidine-Based Ligands for the Muscarinic Cholinergic Receptor", Journal of Medicinal Chemistry, 1990, vol. 33, No. 4, pp. 1128-1138.
Schulman et al., "Recognition of Cholinergic Agonists by the Muscarinic Receptor. 1. Acetylcholine and Other Agonists with the NCCOCC Backbone", Journal of Medicinal Chemistry, 1983, vol. 26, No. 6, pp. 817-823.
Seeger et al., "M2 Muscarinic Acetylcholine Receptor Knock-Out Mice Show Deficits in Behavioral Flexibility, Working Memory, and Hippocampal Plasticity",The Journal of Neuroscience, 2004, vol. 24, No. 45, pp. 10117-10127.
Showell et al., "Synthesis and In Vitro Biological Profile of All Four Isomers of the Potent Muscarinic Agonist 3-(3-Methyl -1,2,4-Oxadiazol-5-yl)-1-Azabicyclo [2.2.1] Heptane", Journal of Medicinal Chemistry, 1992, vol. 35, No. 5, pp. 911-916, Abstract Only.
Showell et al., "Tetrahydropyridyloxadiazoles: Semirigic Muscarinic Ligands", Journal of Medicinal Chemistry, 1991, vol. 34, p. 1086.
Silverman, "The Organic Chemistry of Drug Design and Drug Action", Elsevier Academic Press, Second Edition, 2004, pp. 30-31.
Spalding et al., "Discovery of an Ectopic Activation Site on the M1 Muscarinic Receptor", Molecular Pharmacology, 2002, vol. 61, No. 6, pp. 1297-1302.
Street et al., "Synthesis and Biological Activity of 1,2,4-Oxadiazole Derivatives: Highly Potent and Efficacious Agonists for Cortical Muscarinic Receptors", Journal of Medicinal Chemistry, 1990, vol. 33, No. 10, pp. 2690-2697.

(56) References Cited

OTHER PUBLICATIONS

Tecle et al., "A Rationale for the Design and Synthesis of M1 Selective Muscarinic Agonists", Bioorganic & Medicinal Chemistry Letters, 1992, vol. 2, No. 8, pp. 821-826.

Tejada et al., "Design and Synthesis of Novel Derivatives of the Muscarinic Agonist Tetra (ethylene glycol)(3-methoxy-1,2,5-thiadiazol-4-y) [3-(1-Methyl-1,2,5,6-tetrahydropyrid-3-yl)-1,2,5-thiadiazol-4-yl] Ether (CDD-0304): Effects of Structural Modifications on the Binding and Activity of Muscarinic Receptor Subtypes and Chimeras", Journal of Medicinal Chemistry, 2006, vol. 49, No. 25, pp. 7518-7531.

Tzavara et al., "Dysregulated Hippocampal Acetylcholine Neurotransmission and Impaired Cognition in M2, M4 and M2/M4 Muscarinic Receptor Knockout Mice", Molecular Psychiatry, 2003, vol. 8, pp. 673-679.

Tzavara et al., "M4 Muscarinic Receptors Regulate the Dynamics of Cholinergic and Dopaminergic Neurotransmission: Relevance to the Pathophysiology and Treatment of Related Central Nervous System Pathologies", The FASEB Journal, 2004, vol. 18, No. 12, pp. 1410-1412.

Wamoff et al., "Heterocyclische β-Enaminoester: 171. Synthese and Eigenschaften des 2-Amino-3-Äthoxycarbonyl-1,4,5,6-Tetrahydropyridins", Comminications, Synthesis, 1975, pp. 426-427.

Ward et al., "1,2,5-Thiadiazole Analogues of Aceclidine as Potent M1 Muscarinic Agonists", Journal of Medicinal Chemistry, 1998, vol. 41, No. 3, pp. 379-392.

Weinstock et al., "General Synthetic System for 1,2,5-Thiadiazoles", Journal of Organic Chemistry, 1967, vol. 32, No. 9, pp. 2823-2828, Abstract Only.

Wess et al., "Stimulation of Ganglionic Muscarinic M1 Receptors by a Series of Tertiary Arecaidine & Isoarecaidine Esters in the Pithed Rat", European Journal of Pharmacology, 1987, vol. 134, pp. 61-67.

Zhang, "Multiple Muscarinic Acetylcholine Receptor Subtypes Modulate Striatal Dopamine Release, as Studied with M1-M5 Muscarinic Receptor Knock-Out Mice", The Journal of Neuroscience, 2002, vol. 22, No. 15, pp. 6347-6352.

\* cited by examiner

MUSCARINIC AGONISTS AS ENHANCERS OF COGNITIVE FLEXIBILITY

CROSS-REFERENCE TO RELATED APPLICATIONS

This application is a 35 U.S.C. X371 United States National Stage Entry of International Patent Application PCT/US2012/035775 filed Apr. 30, 2012, which claims the benefit of U.S. provisional patent application Ser. No. 61/481,150 filed Apr. 29, 2011, and Ser. No. 61/510,570 filed Jul. 22, 2011, the entire disclosure of which are expressly incorporated herein by reference.

STATEMENT REGARDING FEDERALLY SPONSORED RESEARCH

This invention was made with government support under AG02454, AG027951, and HD055751 awarded by the National Institutes of Health. The Government has certain rights in the invention.

TECHNICAL FIELD AND INDUSTRIAL APPLICABILITY OF THE INVENTION

This invention is directed to methods for enhancing cognitive functions in subjects in need thereof.

BACKGROUND

There is no admission that the background art disclosed in this section legally constitutes prior art.

Although a number of treatments are available to treat the symptoms of mental disorders, relatively few efforts have focused on developing compounds that can improve cognitive function. While recent advances have been made in the understanding of the cholinergic nervous system and the receptors therein, there is still a need to develop compositions which would have a positive effect on a subject's cognitive functions.

One avenue of research being pursued involves cholinergic receptors which are proteins embedded in the cell membrane that respond to the chemical acetylcholine. Cholinergic receptors are subdivided into the nicotinic and muscarinic receptor families. Muscarinic receptors mediate a variety of physiological responses to the neurotransmitter acetylcholine in the central and peripheral nervous systems.

The muscarinic receptors represent a family of five subtypes. One subtype, $M_1$ muscarinic receptors, plays a role in learning and memory function in the brain and regulates gastric acid secretion in the stomach. While an $M_1$ agonist profile could provide efficacy in a broad range of symptomatic domains including enhancement of cognitive function, the development of selective muscarinic agonists has been hindered by the high degree of homology among the five receptor subtypes.

It is difficult to predict whether a muscarinic agonist will have a beneficial result. Efforts to develop muscarinic agonists for the treatment of neurological disorders have been hampered by the high degree of amino acid homology within the binding pocket of muscarinic receptors. While many compounds have been developed with reported selectivity, relatively few compounds have been identified that selectively activate $M_1$ and/or $M_4$ receptors. This is a particular concern in developing treatments that will enhance cognitive function, rather than only ameliorate functional deficit or impairment.

One of the co-inventors herein has developed different muscarinic agonists, which are claimed in U.S. Pat. Nos. 5,403,845; 5,175,166; 5,726,179; 6,096,767; 6,211,204 B1; 6,369,081 B1; 6,376,675 B2; and 6,602,891 B2; and in PCT patent applications Nos. WO/2007/075397 claiming priority to U.S. Ser. No. 60/754,529); PCT/US08/003637 (claiming priority to U.S. Ser. No. 60/919,800), which are expressly incorporated herein by reference. Also, muscarinic agonists are claimed in U.S. Pat. No. 5,618,818 which is owned by the same assignee as herein.

However, to date, there are no pharmacological agents that specifically target muscarinic receptor subtypes, leaving unanswered whether activation of muscarinic receptor subtypes enable cognitive flexibility.

In view of the foregoing, it would be desirable to provide muscarinic agonists that result in the selective activation of muscarinic receptors, particularly so that undesirable side effects are minimized during treatment.

Thus, there is a need for muscarinic agonists with activity at $M_1$ receptors which then would useful in the treatment of Alzheimer's disease and schizophrenia, and other cognitive impairment disorders.

There is also a need for treatments that activate $M_1$ receptors which enhance memory function and the various domains of cognitive flexibility.

SUMMARY

In one aspect, there is described herein a method for positively affecting cognitive functions in a subject, including, in particular, such cognitive functions as: working memory and cognitive flexibility.

In another aspect, there is provided a method for the prevention and/or treatment of working memory and/or cognitive flexibility deficit related conditions and/or enhancements thereof in a subject. In certain embodiments, treatment includes enhancing one or more of working memory and cognitive flexibility.

In another aspect, there is provided herein a method for the treatment of a wide variety of neurologic disease states and other disease states or clinical conditions of related etiology. One of skill in the art would be capable of identifying and evaluating the impairment in a cognitive function in the individual.

In certain embodiments, the disease or condition results from defective or malfunctioning $M_1$ receptors in the subject. In certain embodiments, the treatment disease or condition results from suppressed $M_1$ receptor transmission in the subject.

Non-limiting examples include one or more degenerative neurological disorders including, but not limited to: progressive supranuclear palsy; multi-system atrophy; corticobasal ganglionic degeneration; dementia associated with Parkinson's disease, multiple sclerosis, Huntington's disease, amylotrophic lateral sclerosis; dementia with Lewy bodies; focal vascular dementia affecting frontal-striatal and fronto-subcortical neuronal circuits; fronto-temporal dementia; frontal variant of Alzheimer's disease or mild cognitive impairment; and, frontal cortical, striatal, subcortical or cerebellar cerebrovascular disease.

Non-limiting examples also include one or more cognitive dysfunction disorder associated with other neuropsychiatric diseases including, but not limited to: dysexecutive syndrome of schizophrenia; Fragile X disease; chronic alcoholism; traumatic brain injury; Tourette's syndrome; autism spectrum disorders; attention-deficit hyperactivity disorders; and, post-traumatic stress disorder In another broad aspect, there is provided herein use of a pharmaceutical composition generally as described herein below as CDD-0102A, together with pharmaceutically acceptable carriers or excipients, in the methods treatment described herein.

In another broad aspect, there is provided herein a method of treating a subject in need thereof, comprising administering to the subject a therapeutically effective amount of the pharmaceutical composition, thereby treating the subject.

In certain embodiments, the pharmaceutical composition is provided as a plurality of individual dosage forms, and the pharmaceutical composition is provided with a set of instructions directing the administration of at least one of each individual dosage forms so as to improve working memory and/or cognitive flexibility.

The methods of the present invention can be accomplished by the administration of the compounds of the invention (e.g., compositions including CDD-0102A) by enteral or parenteral means. The route of administration can be by oral ingestion (e.g., tablet, capsule form) or intramuscular injection of the compound. Other routes of administration can include intravenous, intraarterial, intraperitoneal, or subcutaneous routes, nasal administration, suppositories and transdermal patches.

There is also provided herein a kit comprising a composition containing a composition comprising CDD-0102A together with instructions directing administration of said composition to a subject in need of treatment and/or prevention of such mental condition thereby to treat and/or prevent mental condition in said subject.

Various objects and advantages of this invention will become apparent to those skilled in the art from the following detailed description of the preferred embodiment, when read in light of the accompanying drawings.

BRIEF DESCRIPTION OF THE DRAWINGS

FIG. 2A: Graph showing mean (±SEM) percent alternation scores. CDD-0102A significantly improved alternation scores at 0.1, 0.3 and 1.0 mg/kg. $*=p<0.05$ vs. saline and $**=p<0.01$ vs. saline.

FIG. 2B: Graph showing mean (±SEM) number of arm choices in delayed alternation test. CDD-0102A did not affect the number arm entries.

FIG. 3A: Graph showing mean (±SEM) trials to criterion on acquisition of a place discrimination. Injection of CDD-0102A had no effect on acquisition.

FIG. 3B: Graph showing mean (±SEM) trials to criterion on switch to a visual cue strategy. CDD-0102A at 0.03 and 0.1 mg/kg facilitated a shift to a visual cue strategy. $**=p<0.01$ vs. SAL-SAL.

FIG. 3C: Graph showing mean (±SEM) perseverative errors committed in the switch to visual cue discrimination. CDD-0102A 0.03 and 0.1 mg/kg significantly decreased perseverative errors. $*=p<0.05$ vs. SAL-SAL, $**=p<0.01$ vs. SAL-SAL.

FIG. 3D: Graph showing mean (±SEM) regressive errors committed in the switch to visual cue discrimination. CDD-0102A 0.03 and 0.1 mg/kg significantly decreased regressive errors. $**=p<0.01$ vs. SAL-SAL.

FIG. 3E: Graphs showing mean (±SEM) never-reinforced errors committed in the switch to visual cue discrimination. CDD-0102A 0.03 and 0.1 mg/kg significantly decreased never-reinforced errors. $*=p<0.05$ vs. SAL-SAL, $**=p<0.01$ vs. SAL-SAL.

FIG. 4A: Graph showing mean (±SEM) trials to criterion on acquisition of a visual cue discrimination. Injection of CDD-0102A had no effect on acquisition.

FIG. 4B: Graph showing mean (±SEM) trials to criterion on switch to a place strategy. CDD-0102A at 0.03 and 0.1 mg/kg facilitated a shift to a place strategy. $**=p<0.01$ vs. SAL-SAL.

FIG. 4C: Graph showing mean (±SEM) perseverative errors committed in the switch to visual cue discrimination. CDD-0102A 0.03 and 0.1 mg/kg significantly decreased perseverative errors. $**=p<0.01$ vs. SAL-SAL.

FIG. 4D: Graph showing mean (±SEM) regressive errors committed in the switch to visual cue discrimination. CDD-0102A 0.03 and 0.1 mg/kg significantly decreased regressive errors. $**=p<0.01$ vs. SAL-SAL.

FIG. 4E: Graph showing mean (±SEM) never-reinforced errors committed in the switch to visual cue discrimination. CDD-0102A treatment did not affect never-reinforced errors.

DETAILED DESCRIPTION

Figure 1:
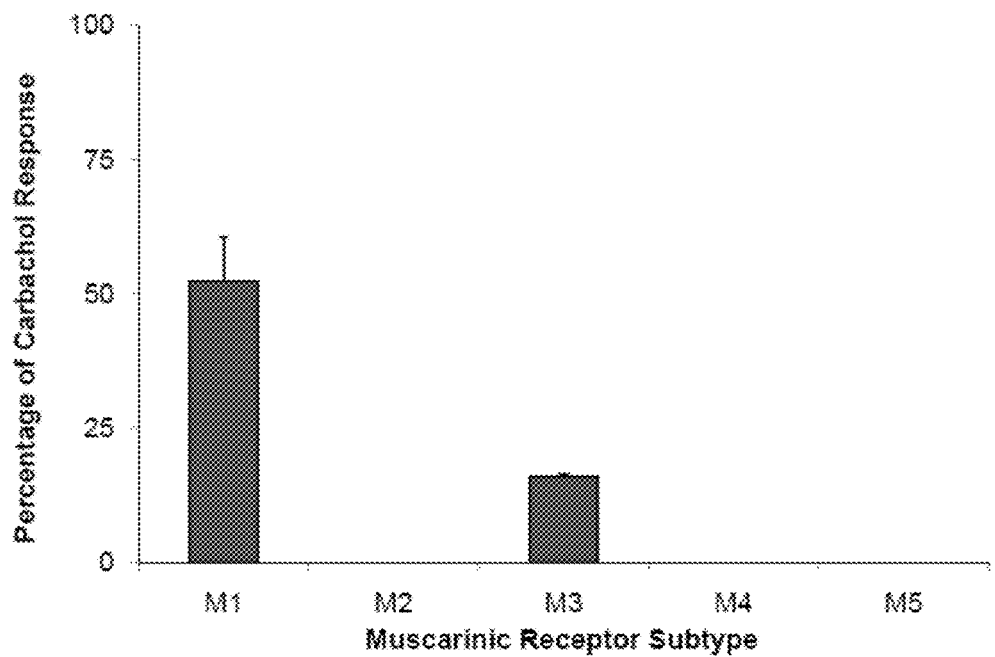
FIG. 1: Graph showing maximal responses of CDD-0102A at muscarinic receptor subtypes, expressed as a percentage of the maximal carbachol response for each receptor subtype. Data represent the mean (±SEM) from at least three experiments each performed in triplicate.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

The terms "improve," "improving" or "improvement" or grammatical variations thereof used in relation to cognitive functions refer to the ability to achieve a measurable increase in performance in relation to tasks used to test these cognitive functions in humans.

The term "memory" is defined as the biological processes of the brain that enable storage and recall of information.

The term "working memory" is defined as a combination of processes of the brain that provide temporary storage and manipulation of information necessary to perform complex cognitive tasks such as learning and reasoning.

The term "concentrate" or grammatical variations thereof refer to the ability of a subject to focus on a particular task without being distracted.

The term "accuracy" or grammatical variations thereof refers to the ability to make correct decisions on tasks used to test these cognitive functions in humans.

The term "effective amount" or "dose" or grammatical variations thereof refers to an amount of agent sufficient to exhibit the desired effects. The effective amount may be determined by a person skilled in the art using the guidance provided herein.

The term "pharmaceutical composition" refers to a composition comprising at least one compound provided by the present disclosure and at least one pharmaceutically acceptable vehicle with which the compound is administered to a subject. "Pharmaceutically acceptable" refers to approved or approvable by a regulatory agency of a federal or a state government, listed in the U.S. Pharmacopeia, or listed in other generally recognized pharmacopeia for use in mammals, including humans.

The terms "treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder.

"Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the subject. In certain embodiments, "treating" or "treatment" refers to delaying the onset of the disease or disorder or at least one or more symptoms thereof in a subject which may be exposed to or predisposed to a disease or disorder even though that subject does not yet experience or display symptoms of the disease or disorder.

The term "treatment" as used herein also refers to any treatment of a subject, such as a human condition or disease, and includes: (1) inhibiting the disease or condition, i.e., arresting its development, (2) relieving the disease or condition, i.e., causing the condition to regress, (3) stopping the symptoms of the disease, and/or (4) enhancing the conditions desired.

The term "therapeutically effective amount" refers to the amount of a compound that, when administered to a subject for treating a disease or disorder, or at least one of the clinical symptoms of a disease or disorder, is sufficient to affect such treatment of the disease, disorder, or symptom. A "therapeutically effective amount" can vary depending, for example, on the compound, the disease, disorder, and/or symptoms of the disease or disorder, severity of the disease, disorder, and/or symptoms of the disease or disorder, the age, weight, and/or health of the subject to be treated, and the judgment of the prescribing physician. An appropriate amount in any given instance can be readily ascertained by those skilled in the art or capable of determination by routine experimentation.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and the claims of this specification the word "comprise" and variations of the word, such as "comprising" and "comprises" is not intended to exclude other additives, components, integers or steps.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions described herein encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The term "combination preparation" comprises both true combinations, meaning medicaments physically combined in one preparation such as a tablet or injection fluid, as well as a "kit-of-parts" comprising medicaments in separate dosage forms, together with instructions for use, optionally with further means for facilitating compliance with the administration of the component compounds, e.g., label or drawings. With true combinations, the pharmacotherapy by definition is simultaneous. The contents of "kit-of-parts" can be administered either simultaneously or at different time intervals. Therapy being either concomitant or sequential will be dependent on the characteristics of the other medicaments used, characteristics like onset and duration of action, plasma levels, clearance, etc., as well as on the disease, its stage, and characteristics of the individual subject.

The term "administration in conjunction with" includes that respective formulations are administered, sequentially, separately and/or simultaneously, over the course of treatment of the relevant condition, which condition may be acute or chronic. In some embodiments, the two formulations are administered (optionally repeatedly) sufficiently closely in time for there to be a beneficial effect for the subject, that is greater, over the course of the treatment of the relevant condition, than if either of the two formulations are administered (optionally repeatedly) alone, in the absence of the other formulation, over the same course of treatment. Determination of whether a combination provides a greater beneficial effect in respect off and over the course of treatment of, a particular condition, will depend upon the condition to be treated or prevented, but may be achieved routinely by the person skilled in the art. Thus, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses are administered within 48 hours, e.g., 24 hours, 18 hours, 12 hours, 6 hours, 3 hours, 2 hours, 1 hour, or 30 minutes of each other. The dose of the composition to be administered will depend on the relevant indication, the age, weight and sex of the subject and may be determined by a physician. In one embodiment, the dosage is in a range of from 0.001 mg/kg to 10 mg/kg. The typical daily dose of the active ingredients varies within a broad range and will depend on various factors such as the relevant indication, the route of administration, the age, weight and sex of the subject and may be determined by a physician. In some embodiments, oral and parenteral dosages may be in the range of 0.1 to 1,000 mg per day of total active ingredients.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids.

Pharmaceutically acceptable salts may be obtained using standard procedures well known in the art, for example by mixing a compound of the present invention with a suitable acid, for instance an inorganic acid or an organic acid.

As used herein, the term "medical therapy" intendeds to include prophylactic, diagnostic and therapeutic regimens carried out in vivo or ex vivo on humans or other mammals.

The term "subject" as used herein, refers to an animal, for example, a mammal, such as a human, who has been the object of treatment, observation or experiment.

General Description

A number of neurological disorders are associated with a dysexecutive syndrome, characterized by executive dysfunction; frontal type of cognitive symptoms; fronto-striatal cognitive impairment; fronto-subcortical cognitive impairment and characterized by bradyphrenia or slowness of thinking, lack of focused attention, impaired ability to concentrate, plan, handle abstract concepts and shift strategies.

Subjects with dysexecutive syndrome exhibit impairments in neuropsychological tests of cognitive executive functions including, but not limited to, the Wisconsin Card Sorting Test, the Stroop test, Trail Making Tests A and B, the Frontal Assessment Battery, and other tests familiar to neuropsychologists.

Described herein is a drug intervention useful in the treatment of a wide variety of neurologic disease states and other disease states or clinical conditions of related etiology.

According to one aspect, there is provided a use of a composition to improve and/or prevent a decline in human cognitive abilities. The composition includes a therapeutically effective amount of a selective $M_1$ muscarinic agonist. It is to be understood that the term "$M_1$" is also referred to as a "muscarinic acetylcholine receptor $M_1$," "cholinergic receptor," and/or "muscarinic 1." In one embodiment, the compound comprises [5-(3-ethyl-1,2,4-oxadiazol-5-yl)-1,4,5,6-tetrahydropyrimidine], which compound is variously referred to herein as "CDD-0102," "CDD-0102A" and [5-(3-ethyl-1,2,4-oxadiazol-5-yl)-1,4,5,6-tetrahydropyrimidine].

It is to be understood that by the use of the term "compound" that analogs and pharmaceutically acceptable salts or hydrates thereof are also included in the use of the term "compound."

The CDD-0102A compound is a partial $M_1$ muscarinic agonist with low activity at other muscarinic receptor subtypes (see FIG. 1). The CDD-0102A compound is a potentiator of the $M_1$ subtype of muscarinic receptors; and, further, is a selectively potentiator of the $M_1$ receptor relative to other the muscarinic receptors (i.e., $M_2$, $M_3$, $M_4$, $M_5$ subtypes).

By "muscarinic related disorder," it is generally meant a disorder whose symptoms are ameliorated by activating a muscarinic receptor.

By "selectively activating $M_1$ receptors," it is generally meant activating $M_1$ receptors in a subject without substantially affecting (e.g., by activating and/or suppressing) other M subtype receptor activity. These other M subtype receptors are generally understood to include $M_2$, $M_3$, $M_4$ and/or $M_5$ receptors. By "selectively activating $M_1$ receptors" in a subject, such subject does not substantially experience symptoms or the effects that are caused by the other M subtype receptors.

The present invention is based, at least in part, on the inventors' discovery that the selective muscarinic agonist CCD-0102A compound is able to increase behavioral flexibility, which is a critical component of normal cognitive function. The selective muscarinic agonist CCD-0102A compound also has utility in the treatment of neurological disorders involving deficits in behavioral flexibility.

Accordingly, one embodiment is directed to a method for treatment of cognitive and behavioral disorders in warm-blooded vertebrates by administering the selective muscarinic agonist CCD-0102A compound, which compound, when present at effective concentrations in the brain, is now shown herein to be capable of inhibiting or otherwise modulating the activity of one or more muscarinic agonists.

In a related embodiment there is provided method for treatment of cognitive and behavioral disorders in a subject in need of such treatment.

The use of the selective muscarinic agonist CCD-0102A compound, in enhancing behavioral flexibility and reducing perseverative and regressive errors, allows such selective muscarinic agonist CCD-0102A compound to be effective in enhancing behavioral flexibility in a wide variety of neurological disorders.

The selective muscarinic agonist compound CDD-102A is useful to treat a variety of neurological disorders that entail specific cognitive deficits involving a loss of behavioral flexibility and attention.

These deficits are found specifically in degenerative neurological disorders including, but not limited to: progressive supranuclear palsy; multi-system atrophy; corticobasal ganglionic degeneration; dementia associated with Parkinson's disease, multiple sclerosis, Huntington's disease, amylotrophic lateral sclerosis; dementia with Lewy bodies; focal vascular dementia affecting frontal-striatal and frontosubcortical neuronal circuits; fronto-temporal dementia; frontal variant of Alzheimer's disease or mild cognitive impairment; and frontal cortical, striatal, subcortical or cerebellar cerebrovascular disease.

The selective muscarinic agonist compound CDD-102A is also useful to treat cognitive dysfunction associated with other neuropsychiatric diseases including dysexecutive syndrome of schizophrenia; Fragile X disease; chronic alcoholism; traumatic brain injury; Tourette's syndrome; autism spectrum disorders; attention-deficit hyperactivity disorders; and post-traumatic stress disorder.

In another aspect, disclosed herein is a method of increasing the activity of a muscarinic receptor, comprising contacting the receptor with an effective amount of the CDD-102A compound.

In another aspect, disclosed herein is a method of treating a subject suffering from a muscarinic receptor related disorder comprising: identifying a subject in need thereof, and administering to the subject a therapeutically effective amount of the CDD-102A compound.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

EXAMPLES

Methods

Animals

For behavioral studies, male Long-Evans rats were purchased from Harlan (Indianapolis, Ind.) weighing between 325-375 g. Rats were individually housed in plastic cages (20.3 cm×20.3 cm×41.9 cm) in an environmentally controlled room (23° C., 30% humidity) on a 12 h:12 h light:dark cycle (lights on at 7:00 am). After at least four days to acclimate to the colony room, rats were handled for 10 minutes per day for four days to adjust to being handled during training and testing. At the same time rats began to be handled, rats were also food restricted to reduce their weight to 85-90% of their ad libitum weight. Rats had free access to water throughout the experiment. Animal care and use conformed to the guidelines of the National Institutes of Health Guide for the Care and Use of Laboratory Animals, and was approved by the Institutional Laboratory Animal Care and Use Committee at the University of Illinois at Chicago.

For studies of salivation, male Long-Evans rats were purchased from Charles River Laboratories (Wilmington, Mass.) weighing between 250-425 g. Animals were kept in a vivarium on a 12-h light/dark cycle. Humidity was maintained at 30-70%, and temperature was maintained at 20-24° C. All procedures were approved by the Institutional Animal Care and Use Committee at Mithridion, Inc.

Behavioral Testing

All behavioral testing occurred in a cross maze made of translucent black acrylic. Each arm measured 55 cm long, 10 cm wide, and 15 cm in height. A circular food well, with a diameter of 3.2 cm and a depth of 1.6 cm was placed 3 cm from the end of each arm. The maze was placed on a table with a height of 72 cm.

Delayed Spontaneous Alternation.

In this test, rats were placed in the testing room 5 minutes prior to behavioral testing. At the beginning of a session, a rat was allowed to freely choose an arm, but after making a choice, a block was placed into that arm for 30 seconds preventing a rat from entering another arm. The block was a 21.5 cm×12 cm piece of plastic. After the 30 second delay, the block was removed and a rat was allowed to enter another arm. The number and sequence of arm entries was recorded. An arm entry was recorded when all four paws entered an arm. An alternation was defined as entry into four different arms on overlapping quadruple sets of arm entries; e.g., a quadruple set consisting of arm choices A, D, C, B was an alternation but a quadruple set consisting of arm choices A, D, A, C was not. The percent alternation score is equal to the ratio of (actual alternations/possible alternations) multiplied by 100; chance performance on this task is 22.2%. The test session lasted 15 minutes. Rats that made less than 11 arm entries were excluded from the analysis. Thirty minutes before testing, a rat received an i.p. injection of one of the following treatments: 1) saline (n=8); 2) CDD-0102A 0.03 mg/kg (n=8); 3) CDD-102A 0.1 mg/kg (n=8); 4) CDD-0102A 0.3 mg/kg (n=7) or 5) CDD-0102A 1 mg/kg (n=8). CDD-0102A was mixed in sterile saline.

Place—Visual Cue Discrimination Learning and Strategy Switching.

A different group of rats was used for the discrimination learning and strategy switching tests from that used in the delayed spontaneous alternation test. Prior to testing, rats were food-restricted to maintain their weight at 85% of their free-feed weight, handled and trained in the maze to obtain half piece of Froot Loops® cereal in the cross-maze.

Following training, each rat was tested across two consecutive days. In the first experiment each rat had to learn a place discrimination. Rats were started in a pseudorandom manner from one of two different arms such that any start arm was not used more than 3 consecutive trials. The two start arms ("east" and "west") were always opposite each other. A black plastic block was placed in the entrance of the maze arm opposite to that of the start arm, giving the maze a T-shape. Thus, the same two choice arms were used no matter what start arm was used. A rat was started in the stem arm with only one of the two choice arms baited. In the acquisition phase, one choice arm or place was designated the reinforced arm which contained a ½ piece of cereal reinforcement on each trial. In this phase, a rat was required to enter the reinforced arm containing a ½ piece of cereal. If a rat chose the correct arm, the trial was terminated after a rat consumed the cereal piece. If a rat chose the incorrect arm, the trial was terminated after a rat reached the unbaited food well. Black and white visual cues that lined the base and side walls of the choice arms were assigned on a pseudorandom basis to be on the left or right of the start arm so that they occurred in each start arm an equal number of times in blocks of 12 trials. Between trials, the maze, visual cues, and block were wiped down with 2% Quatricide® solution to minimize the animals' ability to use odor cues for discriminations. Between trials, a rat was placed in a holding chamber which was placed on a table next to the maze. The maze was then wiped down and re-baited if necessary. The inter-trial interval was approximately 15 seconds. To minimize the use of intramaze cues the maze was rotated 90° every fourth trial. The criterion for acquisition of the place discrimination was 10 consecutive correct trials.

The day following the acquisition phase, each rat was tested on the switch to the visual cue strategy. In the switch phase, a rat was required to switch strategies from always entering a choice arm based on spatial location to entering a choice arm based on visual cue (black or white). Again, the visual cues were switched in a pseudorandom manner between choice arms so that a particular cue was associated with the same choice arm for a maximum of three consecutive trials and was equally associated with each turn direction across consecutive blocks of 12 trials. The learning criterion in the switch phase was also 10 consecutive correct arm choices. Thirty minutes prior to each test phase, rats received an i.p. injection of the designated treatment for that phase. The rats were divided into the following groups: 1) saline—saline (n=9); 2) saline—CDD-0102A 0.003 mg/kg (n=7); 3) saline—CDD-0102A 0.03 mg/kg (n=9); 4) vehicle—CDD-0102A 0.1 mg/kg (n=8); 5) CDD-0102A 0.03 mg/kg-saline (n=8); or 6) CDD-0102A 0.01 mg/kg-saline (n=7).

In a separate experiment, the effect of CDD-0102A on initial learning of a visual cue strategy and switch to a place strategy was determined. All other aspects of the testing procedure were as described above. The treatment groups in this experiment were as follows: 1) saline—saline (n=8); 2) saline—CDD-0102A 0.003 mg/kg (n=7); 3) saline—CDD-0102A 0.03 mg/kg (n=7); 4) vehicle—CDD-0102A 0.1 mg/kg (n=8); 5) CDD-0102A 0.03 mg/kg-saline (n=7); or 6) CDD-0102A 0.01 mg/kg-saline (n=8).

In the switch phase of each experiment, the errors committed were separated into different categories and analyzed. The errors were separated into perseverative, regressive and never-reinforced errors. In the place acquisition and shift to visual cue experiment, for half the trials a rat had to enter the arm that was in the opposite place as the arm that was reinforced in the place acquisition phase. For example, a rat might have to learn to always enter the "north" arm in the place acquisition phase. In the shift to visual cue phase, a rat now had to always enter the arm with the black visual cue. Thus, when the black visual cue was in the "south" arm, a rat had to switch from choosing the "north" arm and enter the "south" arm. These trials were used to analyze the perseverative and regressive errors. These trials were initially separated into consecutive blocks of 4 trials each. Perseveration was defined as initially entering the incorrect arm in three or more trials per block. Thus, if a rat was initially choosing the previously correct choice on the majority of trials it was considered perseveration. Once a rat made less than three errors in a block the first time, all subsequent errors were no longer counted as perseverative errors. When perseveration ended, as defined above, the number of errors was counted when a rat reverted back to the previously correct choice on those trials that required the opposite turn as on the place version. These errors are referred to as regressive errors. During the shift, a third type of error could be made if a rat entered the arm that contained neither the presently correct visual cue nor the previously correct location. For example, in half the trials the presently correct visual cue (e.g., black) was in the previously correct spatial location (e.g., "north" arm) and if a rat chose the "south" arm this would count as an error. These errors are referred to as never-reinforced errors because a rat was never reinforced for this choice on either acquisition or switch phases.

These same types of errors were calculated in a similar manner for the experiment in which rats first learned a visual cue strategy and then switched to a place strategy.

Statistical Analysis

In the spontaneous alternation task, a one-way analysis of variance was used to identify differences in percent alternation scores and number of arm entries across groups. Newman-Keuls post-hoc tests were used to compare treatment and control group measures. In the discrimination learning tests, one-way analyses of variance were used to identify differences in trials to criterion for acquisition and strategy switching. Separate analyses of variance were carried out to determine group differences in perseverative, regressive, and never-reinforced errors. Newman-Keuls post-hoc tests were used to compare differences between treatment groups.

Salivation Studies

Salivation was quantified in rats following i.p. administration of CDD-0102A. Rats were first anesthetized with isoflurane, and then dosed with CDD-0102 by i.p. injection. Anesthesia was maintained by a nose cone that delivered 1.5-2.5% isoflurane in 500 ml/minute of oxygen. CDD-0102A was dissolved in phosphate-buffered saline and the injection volume was 2 ml/kg. The hind limbs of anesthetized animals were taped to the top of an incline (25° grade) so that the animal was oriented with its head near the bottom of the slope and its dorsal-surface oriented upward. Body temperature was monitored by a rectal thermometer, and maintained at 36-38° C. by a heating pad. The animal's nose was inserted into a nose cone for maintaining anesthesia while the entire mouth remained outside this nose cone.

Pre-weighed filter paper (approximately 5×5 cm) was placed underneath the mouth to absorb the draining saliva. After 5 minutes, the saliva-wetted filter paper was weighed and replaced with fresh, pre-weighed filter paper. Total salivary output was calculated by subtracting the mass of the filter paper from the combined mass of paper plus saliva as collected over 60 minutes.

Results

Delayed Spontaneous Alternation

Figure 2A:
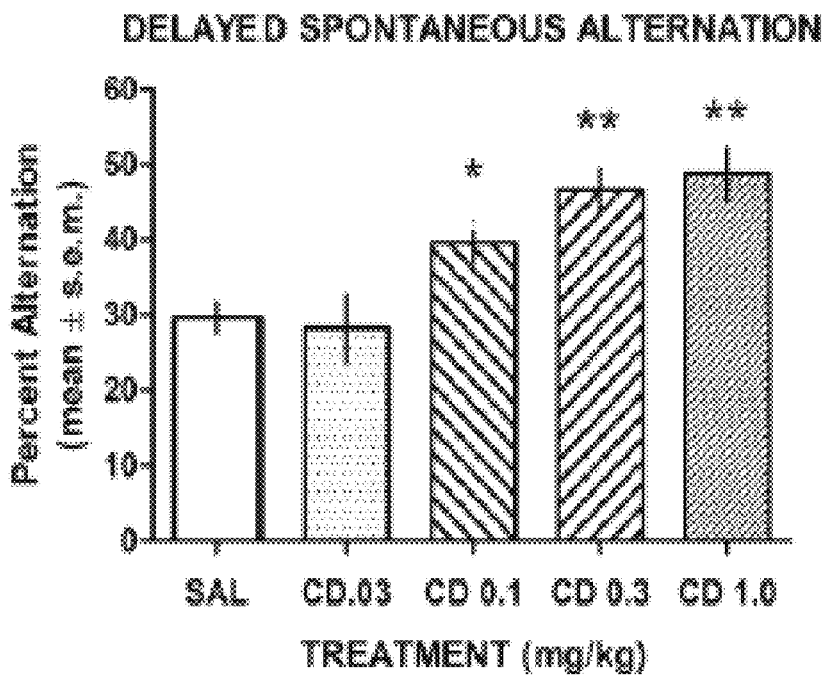
FIGS. 2A-2B: Graphs showing the effect of CDD-0102A on delayed spontaneous alternation. Each rat received an i.p injection of saline (SAL) or one of four doses of CDD-0102A (CD) 30 minutes prior to a delayed spontaneous alternation test in a 4-arm maze. There was a 30 second delay between each arm choice.

Treatments with CDD-0102A significantly enhanced delayed spontaneous alternation in a dose-dependent manner (see FIG. 2A). An ANOVA revealed there was an overall group effect, $F(4, 34)=8.59$, $P<0.01$. Post-hoc tests indicated that CDD-0102A at 0.3 and 1.0 mg/kg significantly enhanced alternation performance compared to that of saline controls and CDD-0102A at 0.03 mg/kg (P values $<0.01$). CDD-0102A at 0.1 mg/kg also significantly enhanced alternation performance compared to that of saline controls and CDD-0102A at 0.03 mg/kg (P values $<0.05$).

Figure 2B:
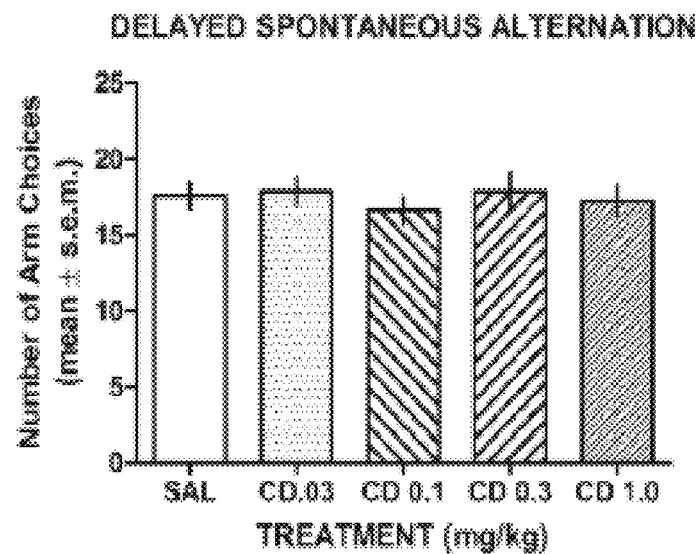

In contrast to alternation scores, CDD-0102A treatment across all doses led to a similar number of arm entries as that of the control group (see FIG. 2B). An ANOVA on the number of arm entries among the groups revealed no significant difference, $F(4, 34)=0.28$, $P>0.05$.

Place Discrimination Acquisition and Switch to Visual Cue Discrimination

Figure 3A:
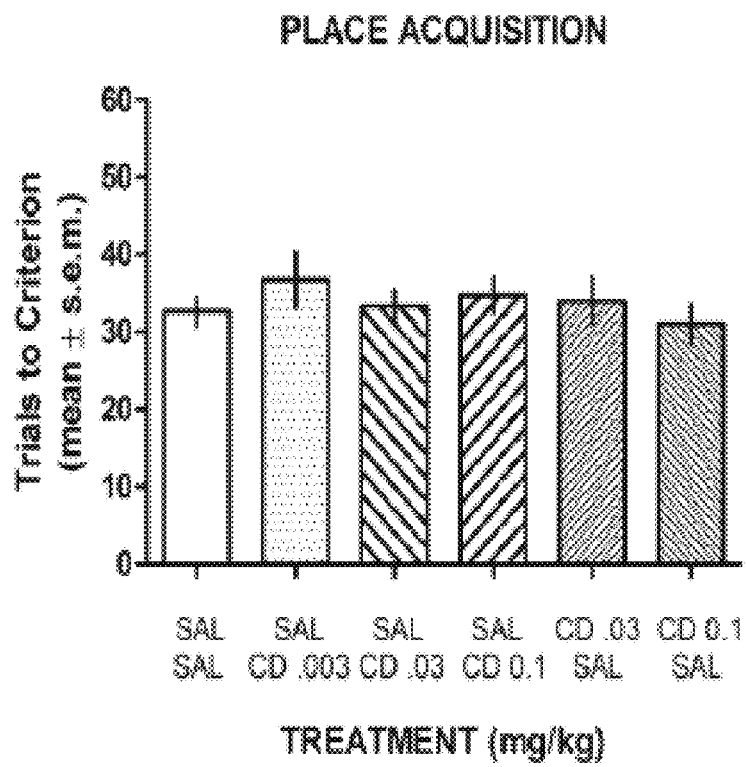
FIGS. 3A-3E: Graphs showing the effect of CDD-0102A on place acquisition and switch to a visual cue discrimination. Each rat received an i.p. injection of saline (SAL) or one of three doses of CDD-0102A (CD) 30 minutes prior to acquisition and switch phases. The treatments in the legends represent the treatment received prior to acquisition (FIGS. 3A-3B) followed by the treatment received prior to the switch phase (FIGS. 3C-3E).
Figure 3B:
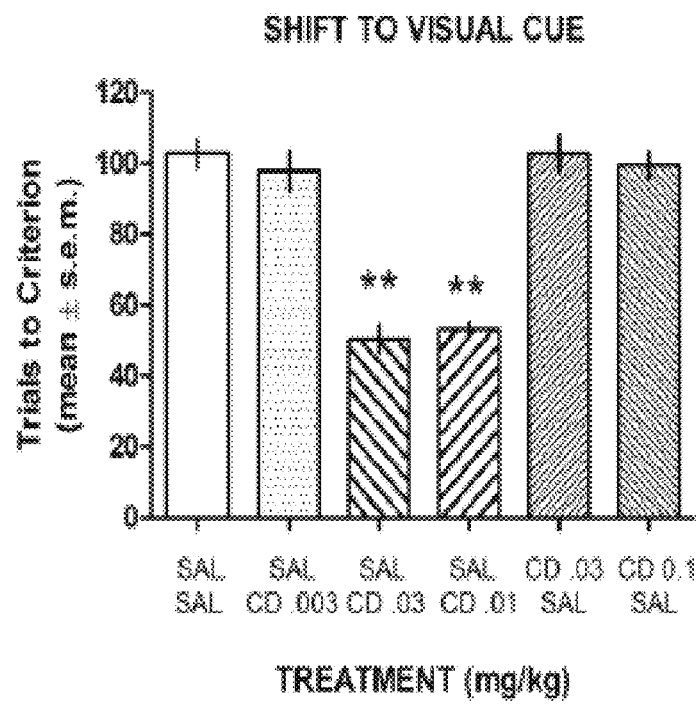

Treatment with CDD-0102A at 0.03 or 0.1 mg/kg 30 minutes prior to acquisition of a place discrimination did not affect learning compared to saline-treated rats (see FIG. 3A). An ANOVA indicated that there was no significant treatment effect on place acquisition, $F(5,42)=0.51$, $P>0.05$. However, there was a significant treatment effect on the switch to the visual cue discrimination, $F(5,42)=37.52$, $P<0.01$. CDD-0102A at doses of 0.03 and 0.1 mg/kg significantly decreased the number of trials to reach criterion as compared to that of all other treatment groups (P values $<0.01$). In contrast, performances of rats treated with CDD-0102A at 0.003 mg/kg were similar to those of saline-treated rats ($P>0.05$). Thus, CDD-0102A improved a shift to a visual cue discrimination in a dose-dependent manner (see FIG. 3B).

Figure 3C:
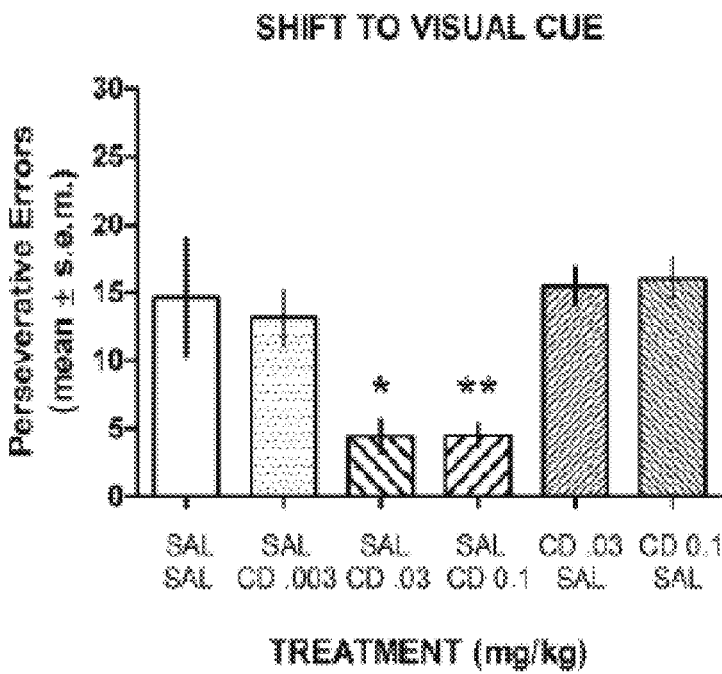
Figure 3D:
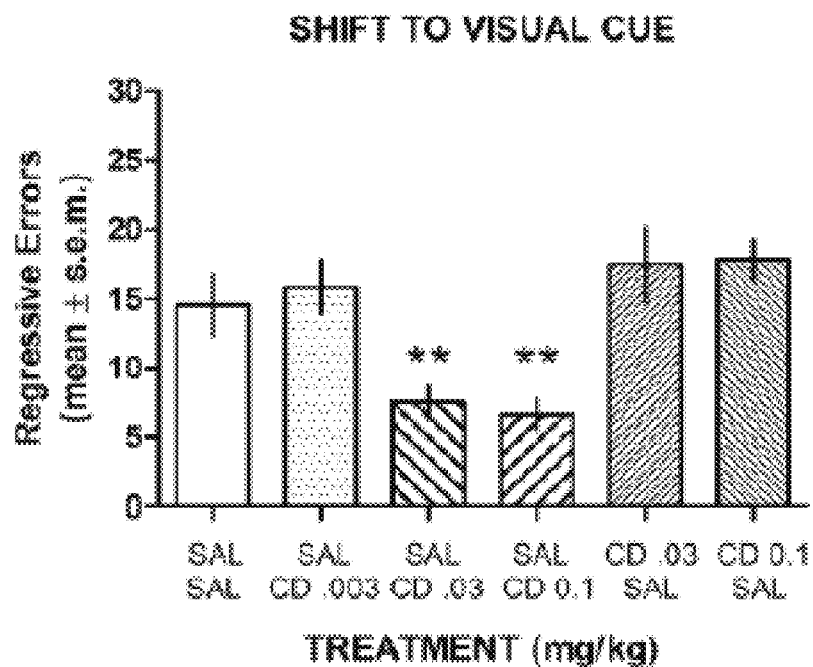
Figure 3E:
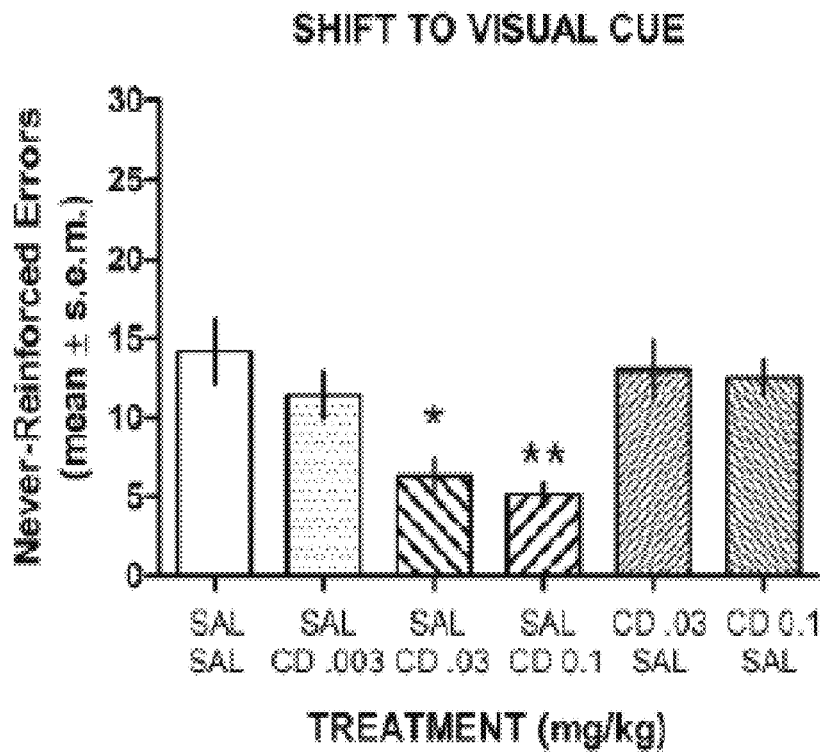

The facilitating effects of CDD-0102A on the switch to a visual cue discrimination resulted from a significant decrease in all three of the error measures (see FIGS. 3C-3E). In particular, CDD-0102A at 0.03 mg/kg significantly reduced perseverative errors compared to that of the lowest dose of CDD-0102A and saline-treated controls (P values $<0.05$). CDD-0102A at 0.1 mg/kg also significantly reduced perseverative errors compared to saline controls and the lowest dose of CDD-0102A (P values $<0.01$). CDD-0102A at 0.03 or 0.1 mg/kg also significantly lessened the number of regressive errors as compared to that of the other treatment groups (P values $<0.01$). In addition, the number of never-reinforced errors committed were significantly greater in saline-treated rats and CDD-0102A 0.003 treatment group compared to that of CDD-0102A at 0.03 mg/kg (P values $<0.05$) and CDD-0102A at 0.1 mg/kg (P values $<0.01$).

Visual Cue Discrimination Acquisition and Switch to Place Discrimination

Figure 4A:
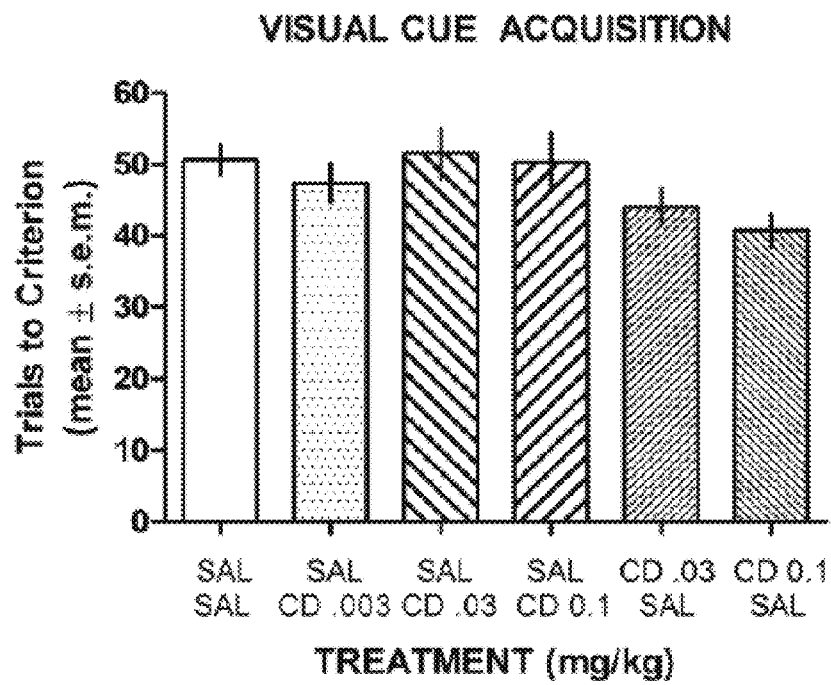
FIGS. 4A-4E: Graphs showing the effect of CDD-0102A on visual cue acquisition and switch to a place discrimination. Each rat received an i.p. injection of saline (SAL) or one of three doses of CDD-0102A (CD) 30 minutes prior to acquisition and switch phases. The treatments in the legends represent the treatment received prior to acquisition (FIGS. 4A-4B) followed by the treatment received prior to the switch phase (FIGS. 4C-4E).
Figure 4B:
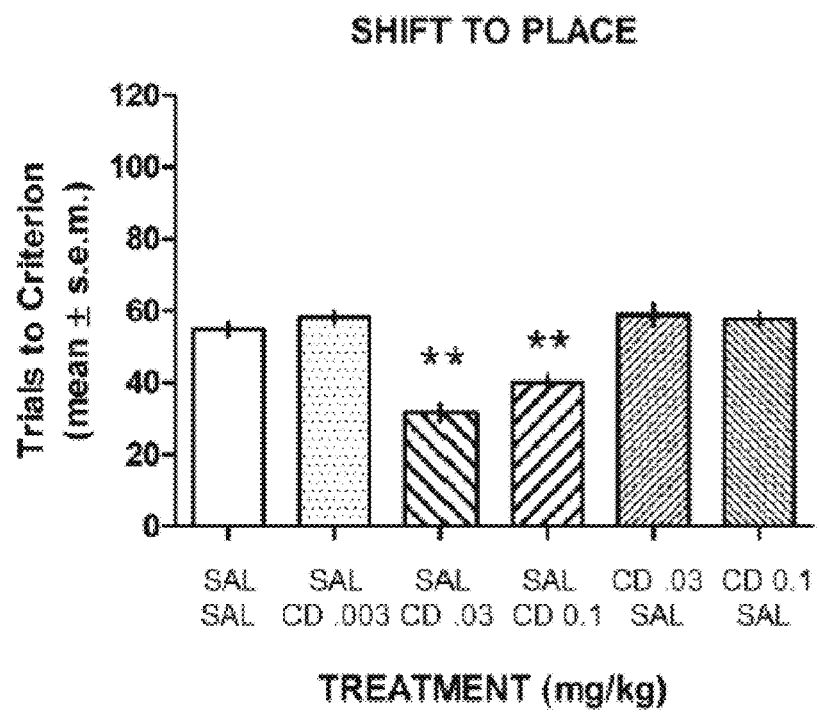

The finding that CDD-0102A treatment enhanced performance on a shift to a visual cue discrimination could reflect a facilitation of strategy switching or a more general enhancement of visual cue learning. To determine between these possibilities, an experiment was carried out that examined the effects of CDD-0102A treatment on acquisition of a visual cue discrimination and shift to a place discrimination. All groups, including those receiving CDD-0102A prior to acquisition, performed in a similar manner in learning a visual cue discrimination (see FIG. 4A). An ANOVA indicated that there was no significant group effect on visual cue acquisition, $F(5,39)=2.10$, $P>0.05$. CDD-0102A treatment did lead to an overall group effect in the switch to the place discrimination, $F(5,39)=24.72$, $P<0.01$. Specifically, CDD-0102A at doses of 0.03 and 0.1 mg/kg significantly enhanced switching to a place strategy as compared to all other treatment groups (P values $<0.01$, see FIG. 4B). CDD-0102A at 0.003 mg/kg had no significant effect on a switch to a place strategy as compared to controls (P values $>0.05$).

Figure 4C:
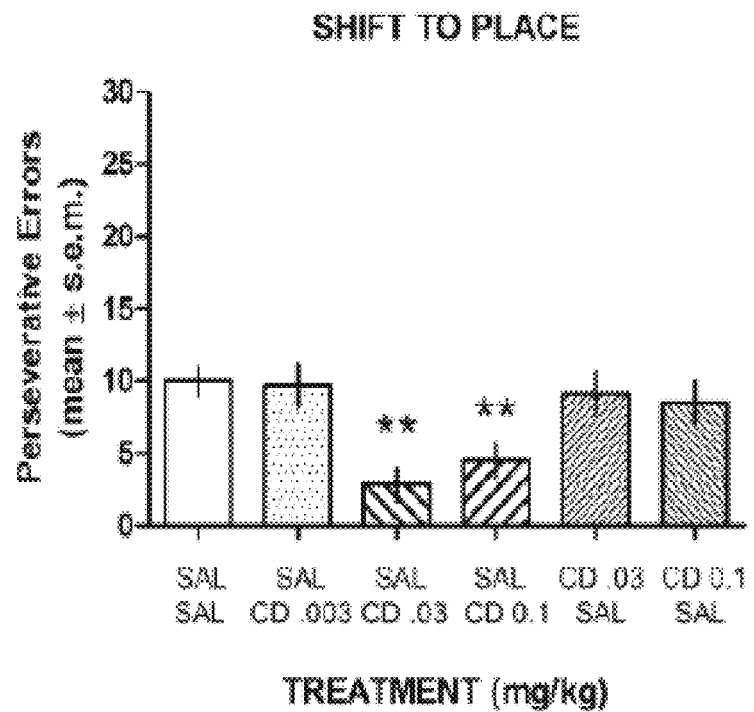
Figure 4D:
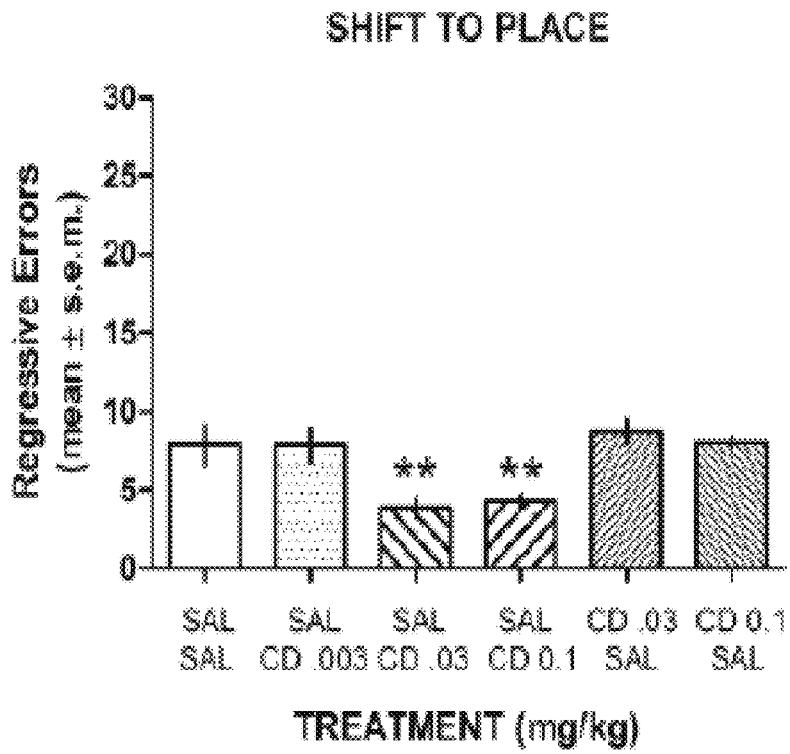
Figure 4E:
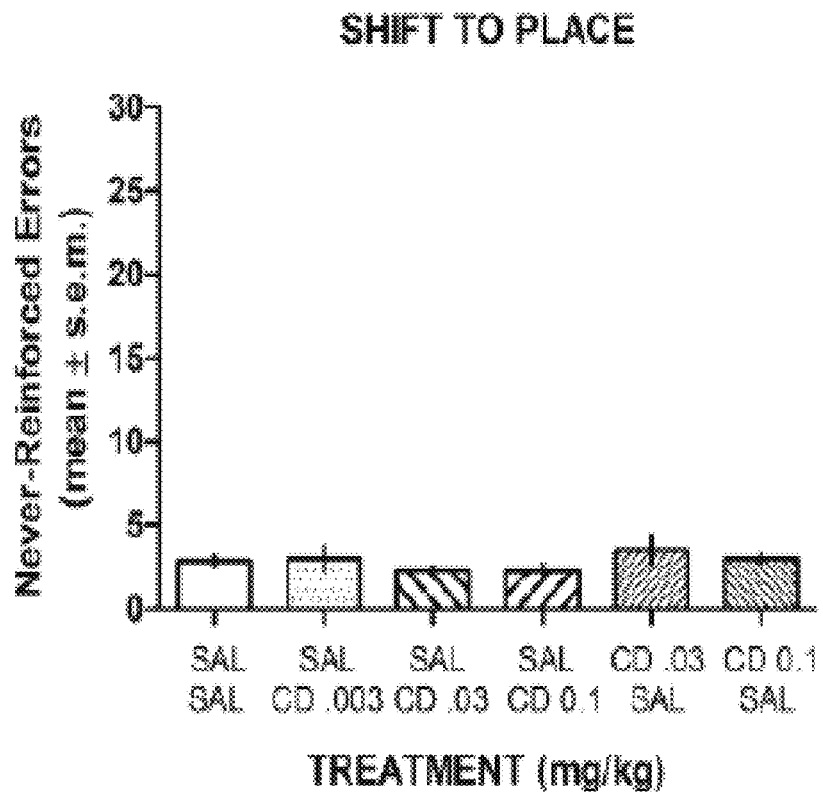

CDD-0102A treatment also affected the errors committed in the switch to the place discrimination (see FIGS. 4C-4E). Compared to all other treatment groups, CDD-0102A at 0.03 and 0.1 mg/kg significantly decreased the number of perseverative errors (P values $<0.01$) and regressive errors (P values $<0.01$). In the switch to the place discrimination, each group made very few never-reinforced errors; thus there was no overall group effect on the number of never-reinforced errors committed, $F(5,39)=0.83$, $P>0.05$.

Salivation

Figure 5:
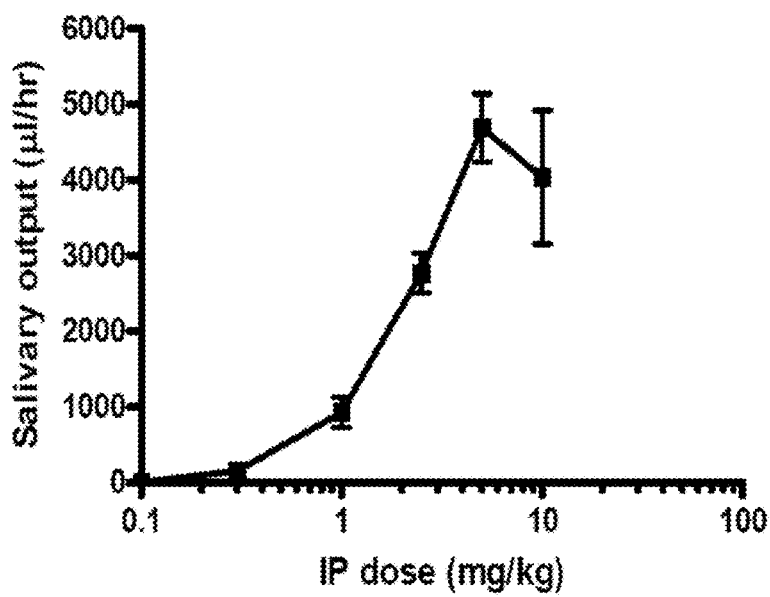
FIG. 5: Graphs showing salivary output over a 60 min time period following i.p. administration of CDD-0102A. Data represent the mean (±SEM) from three animals for each time point.

CDD-0102A was administered to adult, male, Long-Evans rats at doses of 0.1, 0.3, 1, 2.5, 5 and 10 mg/kg by i.p. injection. Salivary output increased as a function of dose over a 60 minute period as shown in FIG. 5. The 0.1 mg/kg dose caused no salivation in rats, while the 5 mg/kg dose produced the most salivation (4,685±449 μl). Salivation from rats dosed with 10 mg/kg was not significantly different from rats given the 5 mg/kg dose ($P>0.5$).

Discussion

CDD-0102A is a selective $M_1$ muscarinic agonist with utility in treating memory deficits associated with Alzheimer's disease. The data herein show that acute treatment with CDD-0102A enhanced both delayed spontaneous alternation and strategy switching in a dose-dependent fashion. CDD-0102A facilitated delayed spontaneous alternation without affecting the number of arms choices, thus showing that the drug enhanced mnemonic processes without any effect on locomotor activity. This task requires a short-term or working memory for recent arm choices.

The present data show that increases in brain acetylcholine release may enhance working memory, in part by activating hippocampal $M_1$ muscarinic cholinergic receptors.

In particular, this is the first demonstration that CDD-0102A alone enhances working memory.

CDD-0102A facilitated strategy switching, regardless of whether a rat switched from a place to visual cue strategy or from a visual cue to a place strategy. In contrast, CDD-0102A treatment did not affect the initial learning of a place or visual cue discrimination. This is the first report of an effect of an $M_1$-selective muscarinic agonist on strategy switching. Strategy switching was found to be surprisingly sensitive to CDD-0102A, being maximal at a dose of 0.03 mg/kg i.p., a dose lower than that required to enhance delayed spontaneous alternation, and much lower than that required to cause salivation.

Further, the data show that a low level of muscarinic receptor occupancy is required for this action. While not wishing to be bound by theory, the inventors herein now believe that, because CDD-0102A was administered systemically, the drug effect on strategy switching is due to activation of multiple brain areas and not limited to the striatum.

CDD-0102A enhanced strategy switching by reducing multiple types of errors. In both experiments, CDD-0102A significantly reduced perseverative errors and regressive errors. Thus, CDD-0102A improved the ability to initially suppress a previously learned strategy and/or generate a new strategy as exhibited by reduced perseveration. CDD-0102A also enhanced the ability to maintain a new strategy once selected as observed by a reduction in the number of regressive errors. Different prefrontal cortex subregions are critical for the initial suppresion of a previously learned strategy as measured by perseverative errors while manipulations of the dorsomedial striatum selectively affects the ability to reliably execute a new strategy once selected. The prefrontal cortex and striatum are two brain areas that have moderate to high densities of $M_1$ muscarinic receptors. Because CDD-0102A treatment reduced both perseverative and regressive errors, this pattern of results shows that CDD-0102A may act at both prefrontal cortex and striatal regions to facilitate initial inhibition of a previously relevant strategy while reliably executing a new strategy once selected.

CDD-0102A significantly reduced never-reinforced errors in the shift from the place to visual cue strategy, but did not affect never-reinforced errors in the shift from the visual cue to place strategy. The differential effect is likely due to rats making few never-reinforced errors in the shift to the place. A rat may make a never-reinforced error because it is trying an alternative, incorrect strategy such as reversing the place choice or shifting to a response strategy (e.g., always turn right). Again, while not wishing to be bound by theory, the inventors herein now believe that the finding that CDD-0102A reduced never-reinforced errors in the shift to the visual cue strategy may indicate that it suppressed the selection of alternative, incorrect strategies and facilitated the selection of the new, correct strategy.

In order to further assess the adverse effect profile of CDD-0102A, salivation was measured in rats over a range of doses comparable to those utilized in the behavioral studies. The lowest dose that produced salivation was 0.3 mg/kg i.p.

The data show that CDD-0102A has beneficial effects on memory and cognitive function at doses that do not produce salivation. The present data also show that CDD-0102A has a broad range of effects on cognition, facilitating both working memory and cognitive flexibility, for example:
significant improvement in memory function was observed at doses of about 0.1 mg/kg and higher; and, doses of about 0.03 mg/kg and about 0.1 mg/kg were effective in enhancing behavioral flexibility.

Example 2

Figure 6:
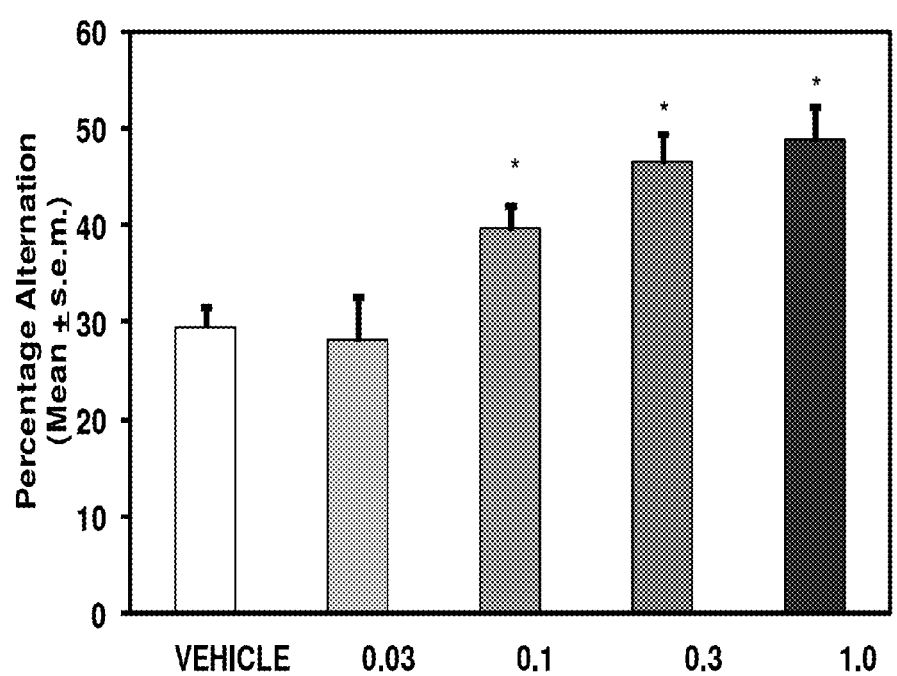
FIG. 6: Graph showing the effects of i.p. injections of CDD-0102A on delayed spontaneous alternation in a modified T-Maze.

CDD-0102A Improves Performance of Normal Rats in the Delayed Spontaneous Alternation Test in a Modified T-Maze Rats were tested in an elevated four-arm maze for their tendency to alternate spontaneously between arms. The animals remember their previous choice and move spontaneously to an alternate arm. By introducing a short delay (30 seconds in this test) their memory for recent events may be tested. CDD-0102A improved performance in a dose-related way in the range 0.1 mg/kg to 1 mg/kg ip (FIG. 6).

This model is very relevant to progressive supranuclear palsy "PSP". This test demonstrates unambiguously that CDD-0102A is able to improve short-term spatial representational memory in ostensibly normal rats, in addition to overcoming a cholinergic deficiency, as set out above.

CDD-0102A Improves Cognitive Flexibility of Normal Rats in an Attentional Set-Shifting Model The beneficial effects of CDD-0102A in the rat model of cognitive flexibility are among the strongest evidence providing the scientific rationale for CDD-0102A in the treatment of PSP. The inventors have developed several models of cognitive flexibility, including the model of attentional set shifting involving an extradimensional set shift described here. The model involves a place-visual cue task. Rats first learned to use a place strategy—always to enter the same arm to receive a food reward. Criterion was set at 10 consecutive correct trials. The following day, rats had to inhibit the place strategy and to learn a new visual cue strategy to receive the reward. Local visual cues in the maze arms included a black board in one arm and white board in the other arm. The cues were switched between the choice arms randomly across trials so the same cue was not always in the same location. The rat had to choose the arm that contained a particular color cue (e.g., black) in order to receive the reward. The criterion again was set at 10 consecutive correct trials.

Figure 7A:
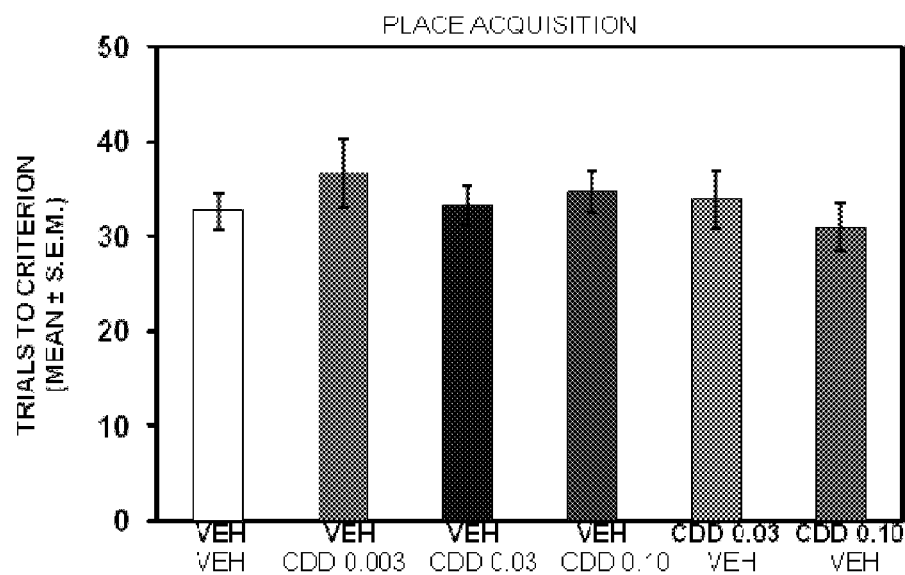
FIG. 7A: Graph where the bold lettering shows the injections (saline vehicle or CDD-0102 in saline) the animals received before the place-cue strategy acquisition. There was no effect of CDD-0102 on acquisition of the place-cue strategy.
Figure 7B:
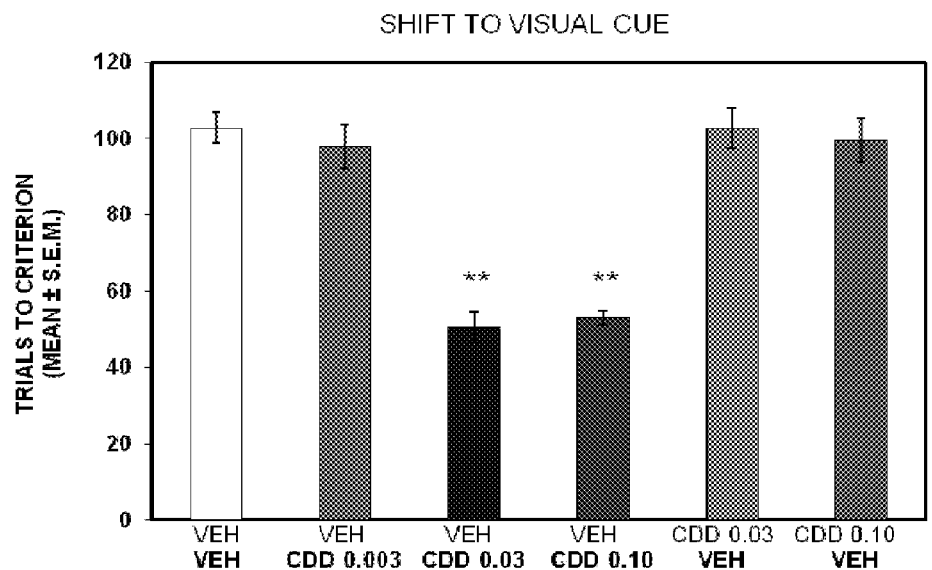
FIG. 7B: Graph showing the results of tests for shifting from a place cue task to a visual cue task. The bold lettering shows the injections (saline vehicle or CDD-0102 in saline) the animals received before the shift. CDD-0102A, at doses of 0.03 and 0.1 mg/kg decreased the number of trials to criterion (10 consecutive correct choices), but only when dosed before the shift, not during the acquisition.

Rats received either saline (N=3) or CDD-0102A at various doses 30 minutes prior to testing. The results are shown in FIGS. 7A-7B. Rats treated with CDD-0102A (0.03 mg/kg or greater dose) before the switch required about half the trials to achieve criterion compared to that of controls.

Figure 8A:
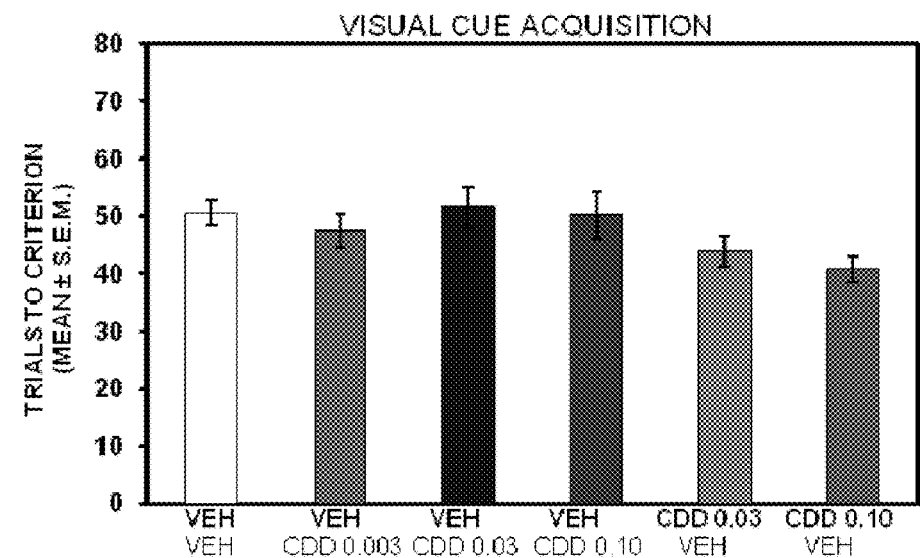
FIG. 8A. The bold lettering shows the injections (saline vehicle or CDD-0102 in saline) the animals received before the visual-cue strategy acquisition. There was no effect of CDD-0102 on acquisition of the visual-cue strategy.
Figure 8B:
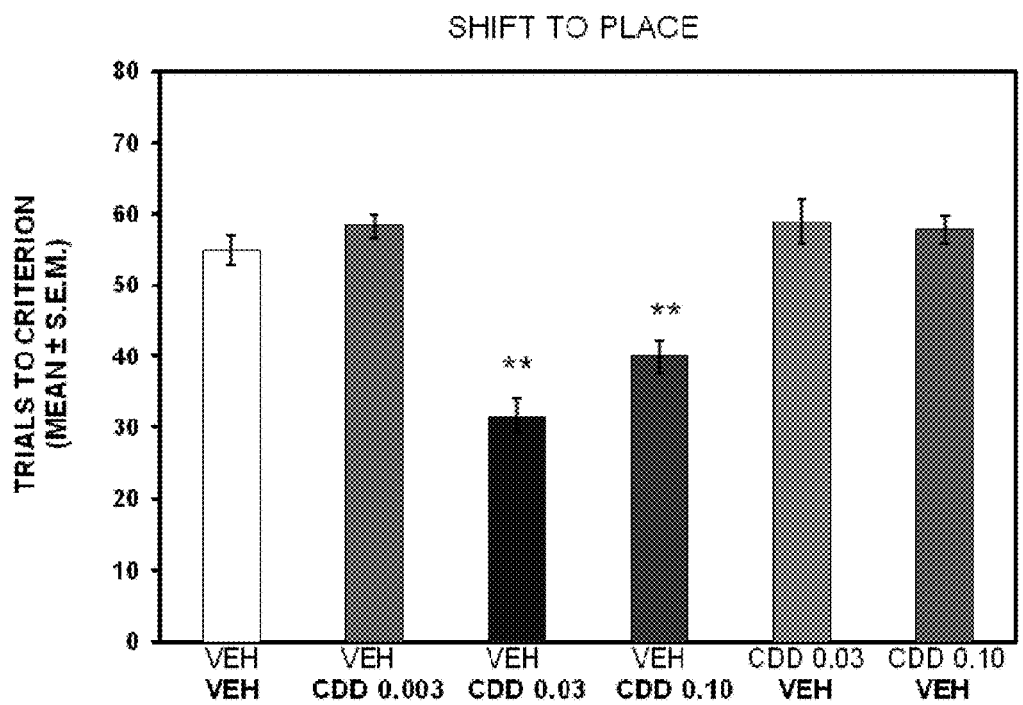
FIG. 8B: Graph showing the results of tests for shifting from a visual cue task to a place cue task. The bold lettering shows the injections (saline vehicle or CDD-0102 in saline) the animals received before the shift. CDD-0102A, at doses of 0.03 and 0.1 mg/kg decreased the number of trials to criterion (10 consecutive correct choices) but only when dosed before the shift, not during the acquisition.

The whole experiment was repeated with the rats learning first a visual cue strategy and then being switched to a place strategy. Results are shown in FIGS. 8A-8B. Rats treated with CDD-0102A (0.03 mg/kg or greater dose before the switch required about half the trials to achieve criterion compared to that of controls.

CDD-0102A therefore improved the ability of the rats to make the attentional set shift. The beneficial effect was on the set shift, not on the acquisition of the first strategy. This was consistent with the effects the selective M1 antagonists in previous experiments, which affected the set shift but not the strategy acquisition.

Further analysis showed that CDD-0102A reduced both the number of perseveration errors and the number of regressive errors.

This test is very relevant for PSP. It has excellent construct validity for the profound impairment of the attentional set shifting exhibited by PSP subjects. The specific cognitive parameter in the rat model improved by CDD-0102A treatment—an extradimensional attentional set shift—is exactly homologous to the impairment exhibited by PSP subjects. Also, the neural substrate of the extradimensional shift in the rat model is part of the striatum, the human counterpart of which is damaged in PSP subjects, and thought to be a cause of the impairment in attentional set shifting.

Also, the impairments in cognitive flexibility contribute strongly to functional impairment in PSP. Thus, both the basic behavioral process and the neural substrates in the animal model are homologous to those in the human disease, PSP, fulfilling a key criterion for construct validity of the animal model.

The cholinergic deficiencies in the striatum in PSP, together with the evidence of the impairment of set shifting by muscarinic M1 receptor blockade by snake venom toxins in the animal model provide additional evidence of the construct validity of this model. Furthermore, the attentional set shifting test (Wisconsin Card Sorting Test) is of the most sensitive test for providing initial evidence of efficacy, and for dose-ranging studies.

CDD-0102A Demonstrates a Good Therapeutic Ratio

Figure 9:
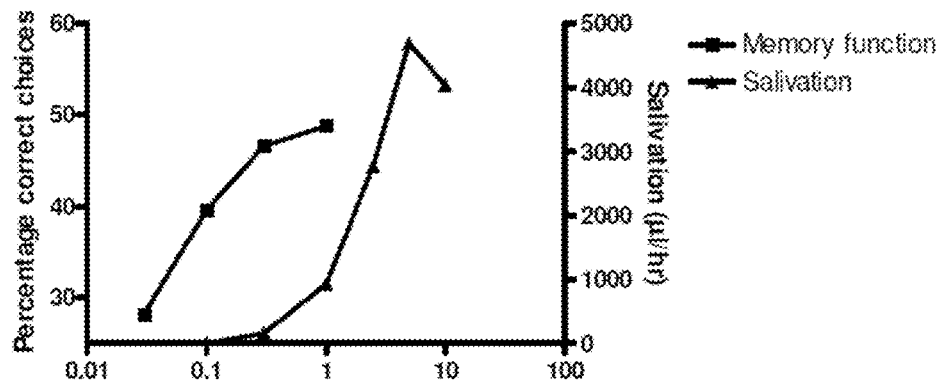
FIG. 9: Graph showing dose responses for spontaneous alternation and salivation.

For a comparison of the effects of CDD-0102A on memory function with effects on salivation, data from two separate experiments were combined as shown in FIG. 9. Significant effects on memory function as measured by spontaneous alternation (adapted from FIG. 6) were observed with CDD-0102A at 0.1, 0.3 and 1.0 mg/kg ip, while salivation was not observed until 0.3 mg/kg. Moreover, CDD-0102A was effective in enhancing learning of a place-visual cue task at a dose of 0.03 mg/kg ip (FIGS. 7A-7B and FIGS. 8A-8B), a dose approximately 100-fold lower than the dose producing half-maximum salivation. These comparisons show a good separation between efficacious doses and those producing adverse effects in rats.

Benefits of CDD-0102A on Disease Processes in PSP

Figure 10:
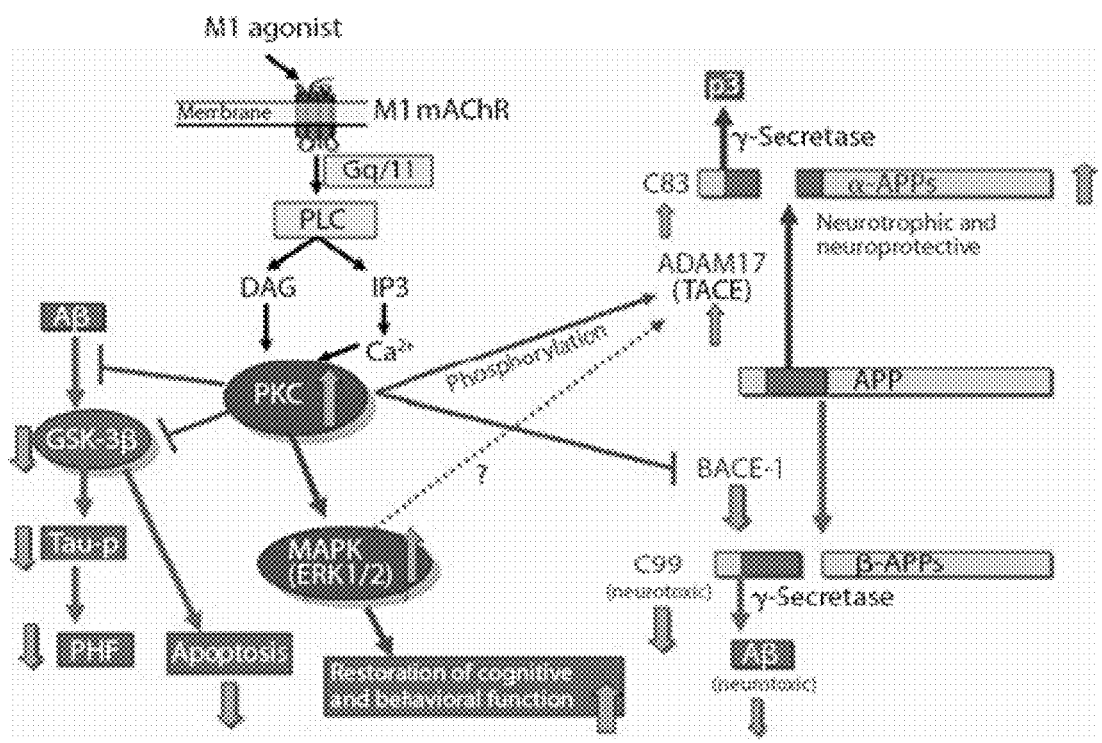
FIG. 10: Schematic illustration showing therapeutic pleiotropic actions of muscarinic M1 agonists as a class on disease mechanisms involved in neurodegenerative diseases.

Muscarinic $M_1$ agonists have pleiotropic actions on neurodegenerative disease processes—see FIG. 10. Several of these muscarinic $M_1$ effects are relevant to PSP and other tauopathies: GSKIIIβ inhibition, PKC activation, Improvement of cognition/behavior, Reduction of Tau phosphorylation, Reduction of PHF formation, and Reduction of apoptosis.

Reduction of tau Hyperphosphorylation by Muscarinic $M_1$ Agonists.

Tau phosphorylation plays a key role in the deposition of tau as aggregates in neurodegenerative diseases, including PSP. Hyperphosphorylated tau prepared from tau aggregates does not bind to microtubules in the normal way of tau. After de-phosphorylation with alkaline phosphatase, normal binding is restored. GSKIIIβ phosphorylates tau, and that PKC inhibits this effect by phosphorylating GSKIIIβ. Muscarinic receptors inhibit GSKIIIβ by phosphorylating it and thereby inhibiting tau phosphorylation in normal and engineered cell lines, primary cell cultures, brain slices, and normal and transgenic mouse models of tauopathies.

CDD-0102A Activates the Inositol Phosphate (IP) Signaling Pathway in the Hippocampus of Rats CDD-0102A was administered intraperitoneally to rats that had been treated 30 minutes previously with lithium chloride (10 mmol/kg). The hippocampi were dissected out 60 minutes later, after euthanizing the animals. The hippocampi were homogenized in buffer and the concentration of inositol-1-phosphate (IP) was determined using a commercial TR-FRET assay (CIS-BIO). In this model, IP derived from the de-phosphorylation of inositol triphosphate produced following muscarinic $M_1$ activation accumulates, its further breakdown being blocked by the lithium chloride treatment. CDD-0102A in the dose range 3 to 30 mg/kg caused a dose-dependent increase in IP, demonstrating that in vivo, it is able to activate the phosphoinositide signaling pathway involved in the pleiotropic effects described herein.

CDD-0102A Inhibits Apoptosis in Cell Lines In Vitro

Figure 11:
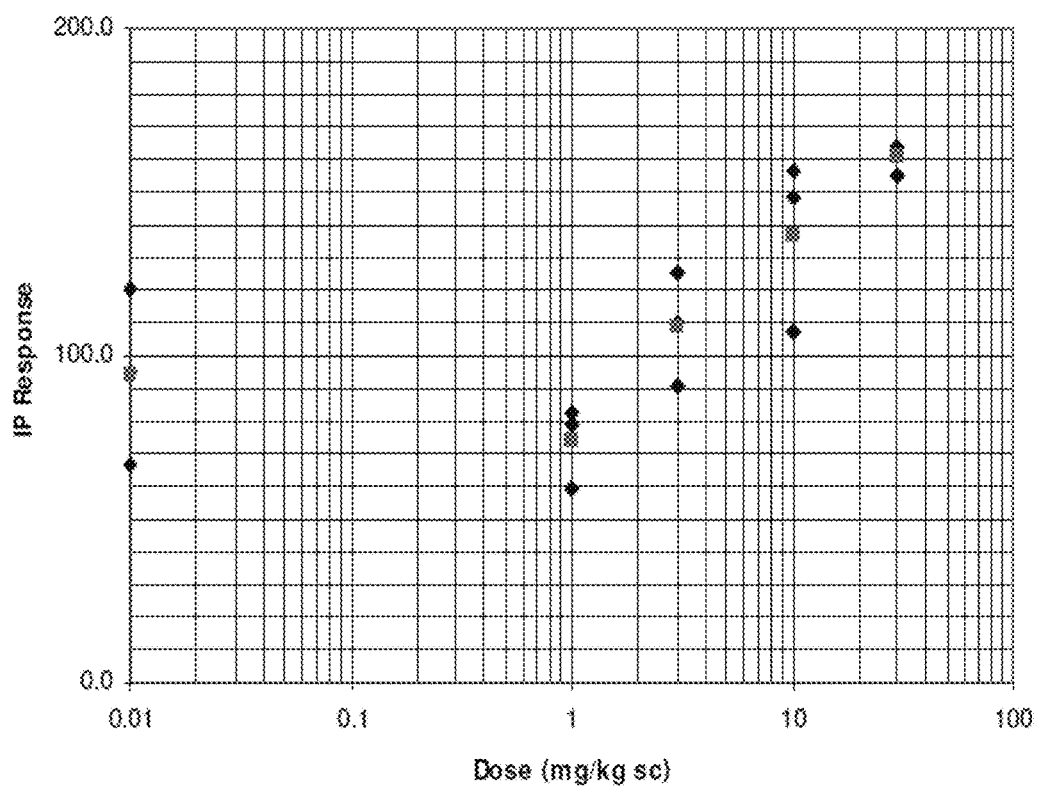
FIG. 11: Graph showing stimulation of IP production in lithium-treated rats by CDD-0102A. The blue symbols are the results of individual rats, the pink symbols being the arithmetic means of the groups.
Figure 12:
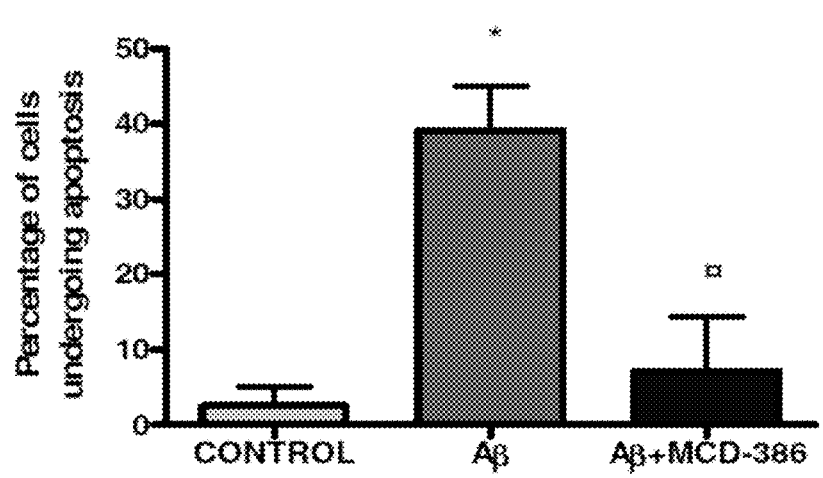
FIG. 12: Graph showing 1 mM CDD-0102A (labeled as "Aβ_MCD-386") protects PC12 cells from apoptosis following treatment with 1 µM Aβ. *Significantly different from control, p<0.05 by ANOVA. Significantly different from Aβ, p<0.05 by ANOVA.

The neuroprotective properties of CDD-0102A also were assessed in cultured neuronal cells. Apoptosis was induced by treating NGF-differentiated PC12 cells with staurosporine or with Aβ. Apoptosis was examined by measuring levels of cleaved caspase-3, and DNA damage was assessed through fluorescence microscopy. CDD-0102A significantly reversed the effects of both staurosporine and Aβ on cleaved caspase-3 levels. DNA damage and neuronal viability (see FIG. 11). This demonstrates that CDD-0102A inhibits not only signaling pathways but also this downstream drug target as identified in FIG. 10. FIG. 12 is a graph showing 1 mM CDD-0102A protects PC12 cells from apoptosis following treatment with 1 μM Aβ.

Examples of Uses

Utilities

The CDD-102A compound is useful in the treatment of memory function symptoms, particularly a memory function, a learning function, and behavioral flexibility function; and more particularly, where the behavioral flexibility function includes one or more of: perseveration errors, regressive errors and never-reinforced errors.

The CDD-0102A compound is useful in the prevention of working memory deficit related conditions.

The CDD-0102A compound is useful in the treatment of working memory deficit related conditions.

The CDD-0102A compound is useful for the enhancement of working memory.

The CDD-0102A compound is useful in the prevention of cognitive flexibility deficit related conditions.

The CDD-0102A compound is useful in the treatment of cognitive flexibility deficit related conditions.

The CDD-0102A compound is useful for the enhancement of cognitive flexibility.

The CDD-102A compounds are useful in the treatment of a subject who has suffered at least one symptom event. Thus, the CDD-102A compounds invention are also useful in the treatment to reduce the likelihood that the subject will further incur such symptoms.

The CDD-102A compounds useful in a subject to reduce the likelihood that the subject will further incur such symptoms.

Routes of Administration

The compounds can be administered by a variety of routes. In effecting treatment of a subject afflicted with disorders described herein, a compound can be administered in any form or mode that makes the compound bioavailable in an effective amount, including oral and parenteral routes. For example, the compounds can be administered orally, by inhalation, or by the subcutaneous, intramuscular, intravenous, transdermal, intranasal, rectal, occular, topical, sublingual, buccal, or other routes. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

Pharmaceutical Compositions

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the subject in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the compound present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampules, disposable syringes or multiple dose vials made of glass or plastic. Preferred compositions and preparations are able to be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a compound or its pharmaceutical salt from about 0.1 to about 10% w/v (weight per unit volume).

Nutraceutical Compositions

The term nutraceutical as used herein denotes the usefulness in both the nutritional and pharmaceutical field of application. Thus, the nutraceutical compositions can find use as supplement to food and beverages, and as pharmaceutical formulations for enteral or parenteral application which may be solid formulations such as capsules or tablets, or liquid formulations, such as solutions or suspensions. As will be evident from the foregoing, the term nutraceutical composition also comprises food and beverages containing CDD-0102A, and optionally one or more components, as well as supplement compositions, for example dietary supplements. The term dietary supplement as used herein denotes a product taken by mouth that contains a "dietary ingredient" intended to supplement the diet. The "dietary ingredients" in these products may include: vitamins, minerals, herbs or other botanicals, amino acids, and substances such as enzymes and metabolites. Dietary supplements can also be extracts or concentrates, and may be found in many forms such as tablets, capsules, softgels, gelcaps, liquids, or powders. They can also be in other forms, such as a bar, but if they are, information on the label of the dietary supplement will in general not represent the product as a conventional food or a sole item of a meal or diet.

Doses

The disorders associated with $M_1$ muscarinic receptors are treated by administering an effective amount of a compound or pharmaceutical composition thereof.

The compounds may be used alone at appropriate dosages defined by routine testing in order to obtain optimal pharmacological effect, while minimizing any potential toxic or otherwise unwanted effects.

An effective amount can be readily determined by the attending diagnostician, as one skilled in the art, by the use of conventional techniques and by observing results obtained under analogous circumstances. In determining an effective amount, the dose of a compound, a number of factors are considered by the attending diagnostician, including, but not limited to: the compound to be administered; the species of mammal—its size, age, and general health; the specific disorder involved; the degree of involvement or the severity of the disorder; the response of the individual subject; the mode of administration; the bioavailability characteristics of the preparation administered; the dose regimen selected; the use of other concomitant medication; and other relevant circumstances.

The specific dose administered is determined by the particular circumstances surrounding each situation. These circumstances can include: the route of administration, the prior medical history of the recipient, the symptom being treated, the severity of the symptom being treated, and the age of the recipient. The recipient subject's attending physician should determine the therapeutic dose administered in light of the relevant circumstances.

Also, it is to be understood that the exact dose may be determined, in accordance with the standard practice in the medical arts of "dose titrating" the recipient; that is, initially administering a low dose of the compound, and gradually increasing the dose until the desired therapeutic effect is observed.

It is to be further understood that the dosage regimen can be selected in accordance with a variety of factors. These include type, species, age, weight, sex and medical condition of the subject; the severity of the condition to be treated; the route of administration; the kidney and liver functions of the subject; and the particular compounds employed. A physician of ordinary skill can readily determine and prescribe the effective amount of the drug required to prevent, counter or arrest the progress of the disease or disorder that is being treated.

In an embodiment, the compounds employed in the methods described herein can be administered in a dose of between about 0.01 mg/kg to about 0.1 mg/kg; about 0.001 mg/kg to about 0.01 mg/kg; about 0.001 to about 0.05 mg/kg; about 0.1 mg/kg to about 1 mg/kg body weight;

about 1 mg/kg to about 5 mg/kg body weight; or between about 5 mg/kg to about 15 mg/kg body weight.

The compounds can be administered in doses of about 0.1 mg, about 1 mg, about 2 mg, about 2.5 mg, about 5 mg, about 10 mg, about 15 mg, about 20 mg, about 25 mg, about 30 mg, about 40 mg, about 45 mg, about 50 mg, about 60 mg, about 80 mg, 100 mg, or any combination thereof. The compounds can be administered once a day or multiple (e.g., two, three, four, five) times per day.

In yet another embodiment, the subject is administered the compounds employed in the methods of the invention at about 1 mg BID (twice a day), about 2 mg BID, about 3 mg BID, about 5 mg BID, about 10 mg BID and about 10 mg TID (three times a day).

In another embodiment, the compounds employed in the methods of the invention can be administered at a dosing regimen that includes progressive or escalating increases in the compound over time of treatment. For example, a subject can be treated with the compound (e.g., such as between about 20 to about 40 mg per day) at a dose of about 2 mg/day at days 1, 2, 3 of treatment; about 4 mg/day at days 4, 5, 6 of treatment; about 6 mg/day at days 7, 8, 9 of treatment; about 20 mg/day at days 13, 14, 15 of treatment and about 30 mg/day at days 16, 17 and 18 of treatment.

The compounds can be administered to the human in a selected dose (e.g., about 10 mg dose taken 3 times a day or about 15 mg dose given as three doses each of which is about 5 mg) while monitoring improvements in the human (e.g., cognition, behavior). If the human does not exhibit any improvement, the compositions employed in the methods can be increased, decreased or stopped until a beneficial effect is observed. For example, if treatment began with three (3) doses of about 10 mg daily and the human subsequently exhibited no apparent improvement, the dose could be increased to three (3) doses of about 15 mg a day, decreased to two (2) doses of about 10 mg a day or treatment could be halted for a single dose, a number of days or weeks and subsequently commenced following the "mini-drug holiday."

"Mini-drug holiday," as used herein, refers to removal of the human from treatment or a decrease in the dose of the compound, followed by re-introduction of the treatment, at a dose equivalent to, below or in excess of the dose the human received prior to the mini-drug holiday.

In yet another embodiment, the invention is a method of treating a human, comprising the step of administering to a human at a dose of about 2 mg per day for days 1, 2 and 3 of treatment, a dose of about 4 mg per day for days 4, 5 and 6 of treatment, a dose of about 6 mg per day for days 7, 8 and 9 of treatment, a dose of about 10 mg per day for days 10, 11 and 12 of treatment, a dose of about 20 mg per day for days 13, 14 and 15 of treatment, a dose of about 30 mg per day for days 16, 17 and 18 of treatment and a dose between about 15 mg to about 80 mg per day for the duration of the treatment or between about 30 mg to about 80 mg per day for the duration of the treatment.

In an additional embodiment, the invention is a method of treating a human, comprising the step of administering to a human at a dosing regimen of at least one member selected from the group consisting of about 1 mg twice a day, about 2 mg twice a day, about 3 mg twice a day, about 5 mg twice a day, about 10 mg twice a day and about 10 mg three times a day.

One skilled in the art can adjust doses of compounds for use in the methods. A suitable dose of a compound for use in a subject can be a titrated dose. For example, the subject would initially receive a low dose, doses would be increased if the low dose was not effective. Doses could be increased about every 3-7 days of treatment, with adjustments as necessary based on side-effects. The doses can be titrated until the maximal tolerated dose or maximally effective dose is determined. Subjects can be maintained at the maximally effective or maximally tolerated dose.

It is to be understood that the compounds are effective in enhancing cognitive function at dosages much lower than previously thought possible or achieved by other types of muscarinic agonists.

In addition, the compounds may be used as adjunctive therapy with known drugs to reduce the dosage required of these traditional drugs, and thereby reduce their side effects.

Kits

In another broad aspect, there is provided herein a kit comprising at least one pharmaceutically effective dosage unit of a CDD-0102A compound, or a pharmaceutically acceptable salt or hydrate thereof;

for administration according to a continuous schedule having a dosing interval selected from one or more of: once daily dosing and/or multiple daily dosing; and, for administration for one or more of: prevention of deterioration of a cognitive function, amelioration of a cognitive function and/or enhancement of a cognitive function in a subject in need thereof; wherein the cognitive function includes one or more of: working memory and cognitive flexibility; and, wherein the administration of the compound gives rise to efficacious treatment without substantially producing $M_2$, $M_3$, $M_4$ and/or $M_5$ subtype receptor activity.

In another broad aspect, there is provided herein a dosage unit, wherein the dosage unit is a formulation comprising from about 0.001 mg/kg to about 10 mg/kg body weight CDD-0102A compound, or a pharmaceutically acceptable salt or hydrate thereof.

In another broad aspect, there is provided herein a dosage unit, wherein the dosage unit is a formulation comprising about 0.01 to about 10 mg/kg body weight CDD-0102A compound, or a pharmaceutically acceptable salt or hydrate thereof.

In another broad aspect, there is provided herein a dosage unit, wherein the dosage unit is a formulation comprising from about 0.1 to about 1.0 mg/kg of body weight CDD-0102A compound, or a pharmaceutically acceptable salt or hydrate thereof.

In another broad aspect, there is provided herein a dosage unit, wherein the dosage unit is a formulation comprising about 0.01 to about 0.1 mg/kg body weight CDD-0102A compound, or a pharmaceutically acceptable salt or hydrate thereof.

In another broad aspect, there is provided herein a dosage unit, wherein the dosage unit is a formulation comprising about 0.001 mg/kg to about 0.01 mg/kg of body weight CDD-0102A compound, or a pharmaceutically acceptable salt or hydrate thereof.

In another broad aspect, there is provided herein a dosage unit, wherein the dosage unit is a formulation comprising about CDD-0102A compound, or a pharmaceutically acceptable salt or hydrate thereof formulated as a daily dosage.

Therefore, it is intended that the invention not be limited to the particular embodiment disclosed herein contemplated for carrying out this invention, but that the invention will include all embodiments falling within the scope of the claims.

What is claimed is:

1. A method of improving a cognitive flexibility function in a human subject having a need thereof, comprising the steps of:

administering to the subject a composition that includes a therapeutically effective amount of at least one M1 agonist compound without substantially producing M2, M3, M4 and/or M5 subtype receptor agonist activity;

wherein the M1 agonist compound is [5-(3-ethyl-1,2,4-oxadiazol-5-yl)-1,4,5,6-tetrahydropyrimidine] (CDD-0102), or a pharmaceutically acceptable salt or hydrate thereof; and wherein the subject does not have a cholinergic deficit, and does have cognitive deficits not associated with a neurodegenerative disorder; and, improving the cognitive flexibility function in the subject.

2. The method of claim 1, wherein the CDD-0102 compound, or a pharmaceutically acceptable salt or hydrate thereof, is administered to the subject in a dose of about 0.01 mg/kg to about 0.3 mg/kg.

3. The method of claim 2, wherein the CDD-0102 compound or a pharmaceutically acceptable salt or hydrate thereof, is administered to the subject in a dose between about 0.01 mg/kg and about 0.3 mg/kg, to thereby effect improved behavioral flexibility in the subject.

4. The method of claim 1, wherein the CDD-0102 compound, or a pharmaceutically acceptable salt or hydrate thereof, is administered to the subject in at least one member selected from the group consisting of a single daily dose, multiple daily doses, two daily doses, three daily doses, four daily doses and five daily doses.

5. The method of claim wherein the CDD-0102 compound, or a pharmaceutically acceptable salt or hydrate thereof, is orally administered to the subject.

6. The method of claim 1, wherein the subject has one or more neuropsychiatric diseases selected from: dysexecutive syndrome of schizophrenia; Fragile X disease; chronic alcoholism; traumatic brain injury; autism spectrum disorders; attention-deficit hyperactivity disorders; and post-traumatic stress disorder.

7. The method of claim 1, wherein the subject is a human child.

8. The method of claim 1, wherein the subject is a human adult.

9. The method of claim 1, wherein the compound is formulated in a nutraceutical composition and is administered orally.

10. The method of claim 1, wherein the administration is chronic.

* * * * *

UNITED STATES PATENT AND TRADEMARK OFFICE
CERTIFICATE OF CORRECTION

PATENT NO. : 9,549,928 B2  
APPLICATION NO. : 14/114646  
DATED : January 24, 2017  
INVENTOR(S) : William S. Messer et al.

Page 1 of 1

It is certified that error appears in the above-identified patent and that said Letters Patent is hereby corrected as shown below:

In the Claims

Column 24, Claim 5, Line 7, after method of claim insert -- 1 --.

Signed and Sealed this
Twenty-eighth Day of March, 2017

Michelle K. Lee
*Director of the United States Patent and Trademark Office*